(12) United States Patent
Harney et al.

(10) Patent No.: US 11,466,245 B2
(45) Date of Patent: Oct. 11, 2022

(54) METHODS FOR CULTURING FILAMENTOUS FUNGI IN FERMENTATION MEDIA

(71) Applicant: The Fynder Group, Inc., Chicago, IL (US)

(72) Inventors: Michael John Harney, Bozeman, MT (US); Richard Eugene Macur, Manhattan, MT (US); Yuval Charles Avniel, Missoula, MT (US)

(73) Assignee: The Fynder Group, Inc., Chicago, IL (US)

( * ) Notice: Subject to any disclaimer, the term of this patent is extended or adjusted under 35 U.S.C. 154(b) by 0 days.

(21) Appl. No.: 17/502,448

(22) Filed: Oct. 15, 2021

(65) Prior Publication Data

US 2022/0106557 A1    Apr. 7, 2022

Related U.S. Application Data

(62) Division of application No. 17/117,715, filed on Dec. 10, 2020, now Pat. No. 11,149,247.

(60) Provisional application No. 62/946,404, filed on Dec. 10, 2019.

(51) Int. Cl.
　　*C12N 1/14*　　(2006.01)
　　*A23L 29/00*　　(2016.01)
　　*A23L 35/00*　　(2016.01)

(52) U.S. Cl.
　　CPC .............. *C12N 1/14* (2013.01); *A23L 29/00* (2016.08); *A23L 35/00* (2016.08); *C12N 2500/02* (2013.01)

(58) Field of Classification Search
　　CPC ............ C12N 1/14; A23L 35/00; A23L 29/00
　　See application file for complete search history.

(56) References Cited

U.S. PATENT DOCUMENTS

| | | | |
|---|---|---|---|
| 2,974,044 A | 3/1961 | Farrow et al. | |
| 5,616,493 A | 4/1997 | Cahoon | |
| 8,999,687 B2 | 4/2015 | Bayer et al. | |
| 9,555,395 B2 | 1/2017 | Araldi et al. | |
| 9,796,989 B2 | 10/2017 | Kozubal et al. | |
| 9,951,307 B2 | 4/2018 | Ross | |
| 9,963,727 B2 | 5/2018 | Medoff et al. | |
| 10,533,155 B2 * | 1/2020 | Kozubal | C02F 3/347 |
| 10,577,579 B2 * | 3/2020 | Kozubal | C12N 1/145 |
| 10,787,638 B2 * | 9/2020 | Kozubal | C02F 3/347 |
| 11,015,168 B2 * | 5/2021 | Kozubal | C12N 1/145 |
| 11,149,247 B2 | 10/2021 | Harney et al. | |
| 2019/0040352 A1 * | 2/2019 | Kozubal | C12N 1/02 |
| 2019/0316077 A1 * | 10/2019 | Kozubal | C12N 1/14 |
| 2019/0316078 A1 * | 10/2019 | Kozubal | C12N 1/14 |
| 2020/0268031 A1 | 8/2020 | Macur et al. | |

FOREIGN PATENT DOCUMENTS

| | | | |
|---|---|---|---|
| WO | WO 2009/050222 | 4/2009 | |
| WO | WO 2017/134664 | 8/2017 | |
| WO | WO 2017/151684 | 9/2017 | |
| WO | WO-2017151684 A1 * | 9/2017 | ............ A23K 10/12 |
| WO | WO 2019/046480 | 3/2019 | |
| WO | WO 2020/176758 | 9/2020 | |

OTHER PUBLICATIONS

Girometta et al., "Physico-Mechanical and Thermodynamic Properties of Mycelium-Based Biocomposites: A Review", Sustainability 2019, 11(1), 281, Published: Jan. 8, 2019 (Year: 2019).*
"Xanthan Gum", https://www.ams.usda.gov/sites/default/files/media/TRXanthanGumHandling042216.pdf (Year: 2016).*
U.S. Appl. No. 17/167,976; U.S. Appl. No. 17/434,577; U.S. Appl. No. 17/502,478 (Year: 2021).*
U.S. Appl. No. 16/990,857 (Year: 2020).*
Basheva et al. "Unique Properties of Bubbles and Foam Films Stabilized by HFBII Hydrophobin," Langmuir, Feb. 2011, vol. 27, No. 6, pp. 2382-2392.
Boswell et al. "Modelling hyphal networks," Fungal Biology Reviews, Apr. 2012, vol. 26, No. 1, pp. 30-38.
Cox et al. "Exceptional stability of food foams using class II hydrophobin HFBII," Food Hydrocolloids, Mar. 2009, vol. 23, No. 2, 366-376.
Fischer et al. "Communicate and Fuse: How Filamentous Fungi Establish and Maintain an Interconnected Mycelial Network," Frontiers in Microbiology, Mar. 2019, vol. 10, Article 619, 20 pages.
Heaton et al. "Analysis of fungal networks," Fungal Biology Reviews, Apr. 2012, vol. 26, No. 1, pp. 12-29.
International Search Report and Written Opinion for International (PCT) Patent Application No. PCT/US20/64208, dated Mar. 2, 2021 14 pages.
Official Action for U.S. Appl. No. 17/117,715, dated Feb. 3, 2021 7 pages Restriction Requirement.
Official Action for U.S. Appl. No. 17/117,715, dated Mar. 11, 2021 14 pages.
Notice of Allowance for U.S. Appl. No. 17/117,715, dated Jun. 18, 2021 8 pages.

* cited by examiner

*Primary Examiner* — Ruth A Davis
(74) *Attorney, Agent, or Firm* — Sheridan Ross P.C.

(57) ABSTRACT

Methods for culturing filamentous fungi, in which the filamentous fungi are grown in a colloid of air and a fermentation medium, are provided. The methods result in more rapid and prolific growth of the filamentous fungus than has been achieved by previous methods. Biomats produced by the methods and air-medium colloids for use in the methods are also provided.

22 Claims, 19 Drawing Sheets

METHODS FOR CULTURING FILAMENTOUS FUNGI IN FERMENTATION MEDIA

CROSS-REFERENCE TO RELATED APPLICATION

This application is a divisional of U.S. patent application Ser. No. 17/117,715, filed 10 Dec. 2020, which claims the benefit of U.S. Provisional Patent Application 62/946,404, filed 10 December 2019, the entireties of both of which are incorporated herein by reference.

FIELD OF THE INVENTION

The present invention relates generally to methods for culturing filamentous fungi, and particularly to methods in which a filamentous fungus is cultured in or on a colloid of a growth medium and air or another user-defined atmosphere, e.g. an atmosphere with a controlled content of oxygen or other constituents to promote fungal growth.

BACKGROUND OF THE INVENTION

The use of filamentous fungi as valuable microbial factories has been exploited in the past, but has generally required significant infrastructure and/or equipment, energy requirements, expensive reagents, and/or significant human resources. Filamentous fungi are well-known for having the greatest metabolic diversity of all microorganisms on Earth, including the ability to produce a wide spectrum of organic acids, enzymes, hormones, lipids, mycotoxins, vitamins, pigments, recombinant heterologous proteins, and other small molecules of interest (e.g. medicinal compounds such as antibiotics, antifungals, and anti-cancer drugs), as well as the ability to degrade many types of recalcitrant materials such as lignocellulose and humic substances in soils.

While widely used, significant challenges to production by submerged fermentation still exist and include important factors such as growth limitation due to the restricted oxygen availability and excessive shear forces generated by agitation. Because oxygen solubility in water is typically about 8 milligrams per liter, oxygen is readily depleted during rapid growth in submerged cultures. Thus, continuous aeration using complex, expensive, and energy-intensive aeration and agitation systems is required to maintain high growth rates. The cultivation of filamentous fungi is even more challenging because the filamentous morphology imparts non-Newtonian rheological behavior that further inhibits oxygen transfer in solution. As culture densities increase, the amount of energy required to aerate and mix the cultures increases nonlinearly, and the energy requirements to aerate dense cultures are thus very high. For many filamentous species, vigorous agitation and aeration of the cultures becomes detrimental to hyphal growth and as a result dramatically decreases growth rates. These and other challenges to submerged fermentation of filamentous microorganisms require innovative solutions to effectively harness the benefits of these organisms in application where resources are limited, e.g. aboard spacecraft or space stations or in challenging terrestrial environments.

More recently, some significant strides have been made in the development of systems and methods for culturing filamentous fungi that do not require active aeration or agitation of the liquid culture, particularly to produce biomats with significant tensile strength. However, the availability of oxygen to the fungus can still present a challenge even in these newer methods and systems. In addition, without wishing to be bound by any particular theory, it is believed that the surface area of the fungus/feedstock interface may also be a limiting factor in the growth of filamentous fungi in these applications.

There is thus a need in the art for systems and methods for culturing filamentous fungi in fermentation media that overcomes these and other drawbacks of submerged fermentation. It is further advantageous for such systems and methods to provide the fungus with greater oxygen availability and/or surface area in contact with a feedstock than previous systems and methods.

SUMMARY OF THE INVENTION

It is one aspect of the present invention to provide a method for culturing a filamentous fungus in a fermentation medium, comprising (a) aerating the fermentation medium to provide an air-medium colloid (AMC); and (b) culturing the filamentous fungus in or on the AMC to form a biomass of the filamentous fungus.

In embodiments, the AMC may be used as a self-contained bioreactor system that isolates the filamentous fungus from a surrounding environment, thus providing a fungal growth system that does not require environmental control.

In embodiments, the AMC may comprise a gelation agent, a viscosity modifier, and/or a humectant or other water activity-reducing component.

In embodiments, the AMC may comprise an inoculum of the filamentous fungus.

In embodiments, the method may further comprise inoculating the AMC with an inoculum of the filamentous fungus.

In embodiments, the AMC may comprise a stabilizer. The stabilizer may, but need not, comprise xanthan gum. A mass ratio of the fermentation medium to the stabilizer in the AMC may, but need not, be between about 100:1 and about 1,000:1. The stabilizer may, but need not, be selected from the group consisting of polysaccharide gums (e.g. xanthan gum, guar gum, locust bean gum, konjac root gum), anionic surfactants (e.g. carboxylates, phosphate esters, sulfate esters, sulfonate esters), cationic surfactants (e.g. primary, secondary, or tertiary amines, quaternary ammonium salts), ceteareth 20, cellulose, diacetyl tartaric esters of mono- and diglycerides (DATEM), diglycerides, emulsifying wax, glycerol monostearate, lecithins, monoglycerides, mustards, non-ionic surfactants (e.g. polysorbate 20, polysorbate 80), soaps, sodium phosphates, sodium stearoyl lactylate, zwitterionic surfactants, saponins, starches, modified starches, plant protein surfactants (e.g. soy protein isolate, pea protein isolate), animal protein surfactants (e.g. casein, whey protein isolate), microparticulates, silica, and combinations and mixtures thereof.

In embodiments, a volume fraction of air in the AMC may be between about 0.05 and about 0.95, between about 0.1 and about 0.9, between about 0.2 and about 0.8, between about 0.3 and about 0.7, between about 0.4 and about 0.6, or about 0.5.

In embodiments, the AMC may be a foam that is stable over at least about 1 day, at least about 2 days, at least about 3 days, at least about 4 days, at least about 5 days, at least about 6 days, at least about 7 days, at least about 8 days, at least about 9 days, at least about 10 days, at least about 11 days, at least about 12 days, at least about 13 days, at least about 14 days, at least about 15 days, at least about 16 days, at least about 17 days, at least about 18 days, at least about 19 days, at least about 20 days, at least about 21 days, at least about 22 days, at least about 23 days, at least about 24 days, at least about 25 days, at least about 26 days, at least about 27 days, at least about 28 days, at least about 29 days, or at least about 30 days.

In embodiments, the filamentous fungus may belong to an order selected from the group consisting of *Ustilaginales, Russulales, Polyporales, Agaricales, Pezizales*, and *Hypocreales*.

In embodiments, the filamentous fungus may belong to a family selected from the group consisting of *Ustilaginaceae, Hericiaceae, Polyporaceae, Grifolaceae, Lyophyllaceae, Strophariaceae, Lycoperdaceae, Agaricaceae, Pleurotaceae, Physalacriaceae, Omphalotaceae, Tuberaceae, Morchellaceae, Sparassidaceae, Nectriaceae*, and *Cordycipitaceae*.

In embodiments, the filamentous fungus may belong to a species selected from the group consisting of *Ustilago esculenta, Hericulum erinaceus, Polyporous squamosus, Grifola fondosa, Hypsizygus marmoreus, Hypsizygus ulmarius, Calocybe gambosa, Pholiota nameko, Calvatia gigantea, Agaricus bisporus, Stropharia rugosoannulata, Hypholoma lateritium, Pleurotus eryngii, Pleurotus ostreatus, Tuber borchii, Morchella esculenta, Morchella conica, Morchella importuna, Sparassis crispa, Fusarium venenatum*, MK7 ATCC Accession Deposit No. PTA-10698, *Disciotis venosa*, and *Cordyceps militaris*.

In embodiments, the method may further comprise, prior to or during step (b), adding a food-grade or food-safe additive to the AMC.

It is another aspect of the present invention to provide a filamentous fungal biomat, produced by a method as described herein.

In embodiments, the biomat may have at least one of the following properties: (a) a thickness of at least about 1.75 mm; (b) a mass of at least about 295 grams per square meter of a top surface area of the AMC; (c) a dry density of at least about 0.20 g/cm$^3$; (d) a tensile strength of at least about 255 kPa; and (e) a carbohydrate content of at least about 47 wt % when dry.

It is another aspect of the present invention to provide a filamentous fungal biomat, having at least one of the following properties: (a) a thickness of at least about 1.75 mm; (b) a mass of at least about 295 grams per square meter of a top surface area of the AMC; (c) a dry density of at least about 0.20 g/cm$^3$; (d) a tensile strength of at least about 255 kPa; and (e) a carbohydrate content of at least about 47 wt % when dry.

In embodiments, a biomat as described herein may comprise a stabilizer.

In embodiments, a biomat as described herein may comprise a food-grade or food-safe additive.

It is another aspect of the present invention to provide a foodstuff, comprising at least a portion of a biomat as described herein.

It is another aspect of the present invention to provide a structural material, comprising at least a portion of a biomat as described herein.

It is another aspect of the present invention to provide a textile material, comprising at least a portion of a biomat as described herein.

It is another aspect of the present invention to provide an air-medium colloid (AMC), comprising a fermentation medium; and air, colloidally dispersed throughout the fermentation medium.

In embodiments, the AMC may further comprise a stabilizer.

For purposes of further disclosure and to comply with applicable written description and enablement requirements, the following references are incorporated herein by reference in their entireties:

Elka S. Basheva et al., "Unique properties of bubbles and foam films stabilized by HFBII hydrophobin," 27(6) *Langmuir* 2382 (February 2011).

Graeme P. Boswell and Fordyce A. Davidson, "Modelling hyphal networks," 26(1) *Fungal Biology Reviews* 30 (April 2012).

Andrew R. Cox et al., "Exceptional stability of food foams using class II hydrophobin HFBII," 23(2) *Food Hydrocolloids* 366 (March 2009).

Monika S. Fischer and N. Louise Glass, "Communicate and fuse: how filamentous fungi establish and maintain an interconnected mycelial network," 10 *Frontiers in Microbiology* 619 (March 2019).

Luke Heaton et al., "Analysis of fungal networks," 26(1) *Fungal Biology Reviews* 12 (April 2012).

While specific embodiments and applications of the present invention have been illustrated and described, it is to be understood that the invention is not limited to the precise configuration and components described herein. Various modifications, changes, and variations which will be apparent to those skilled in the art may be made in the arrangement, operation, and details of the methods and systems of the present invention disclosed herein without departing from the spirit and scope of the invention. It is important, therefore, that the claims be regarded as including any such equivalent construction insofar as they do not depart from the spirit and scope of the present invention.

The advantages of the present invention will be apparent from the disclosure contained herein.

As used herein, "at least one," "one or more," and "and/or" are open-ended expressions that are both conjunctive and disjunctive in operation. For example, each of the expressions "at least one of A, B, and C," "at least one of A, B, or C," "one or more of A, B, and C," "one or more of A, B, or C," and "A, B, and/or C" means A alone, B alone, C alone, A and B together, A and C together, B and C together, or A, B, and C together.

It is to be noted that the term "a" or "an" entity refers to one or more of that entity. As such, the terms "a" (or "an"), "one or more," and "at least one" can be used interchangeably herein. It is also to be noted that the terms "comprising," "including," and "having" can be used interchangeably.

The embodiments and configurations described herein are neither complete nor exhaustive. As will be appreciated, other embodiments of the invention are possible utilizing, alone or in combination, one or more of the features set forth above or described in detail below.

DETAILED DESCRIPTION OF THE INVENTION

Figure 1:
FIG. 1 illustrates four samples of filamentous fungus grown on an air-medium colloid (AMC), according to embodiments of the present invention, and two samples of filamentous fungus grown on a non-colloidal growth medium.

As used herein, the term "biomass" refers to a filamentous fungal structure formed from mycelial growth in an interwoven or intermeshed manner to produce filamentous fungal mass that is coherent.

As used herein, the term "biomat" refers to a filamentous fungal structure having a significantly uniform thickness and a relatively large surface area-to-thickness ratio.

As used herein, unless otherwise specified, the term "colloid" refers to a mixture in which particles of one substance (the "dispersed phase") are dispersed throughout a volume of a different substance (the "dispersion medium"), for example the dispersed phase can comprise or consist of microscopic bubbles, particles, etc. Where the dispersed phase and the dispersion medium of a colloid are specifically identified herein, they are separated by a hyphen, with the dispersed phase identified first, e.g. a reference herein to an "air-medium colloid" refers to a colloid in which air is the dispersed phase and a medium (e.g. a fermentation medium or growth medium) is the dispersion medium.

As used herein, unless otherwise specified, the term "emulsion" refers to a colloid in which both the dispersed phase and the dispersion medium are liquids. Examples of emulsions as that term is used herein include but are not limited to latex, lotion, mayonnaise, and the fat fraction of milk.

As used herein, unless otherwise specified, the term "foam" refers to a colloid in which the dispersed phase is a gas and the dispersion medium is a liquid. Examples of foams as that term is used herein include but are not limited to shaving cream and whipped cream.

As used herein, unless otherwise specified, the term "gel" refers to a colloid in which the dispersed phase is a liquid and the dispersion medium is a solid. Examples of gels as that term is used herein include but are not limited to agar, gelatin, and jelly. In embodiments of the present invention, AMCs in the form of polysaccharide gels may be prepared by, e.g., divalent and monovalent ionic crosslinking, self-assembly, fiber alignment, covalent crosslinking, non-ionic crosslinking, and/or solvent removal crosslinking. AMC gels may be dried, in some embodiments freeze-dried, for storage or transport and then rehydrated for later use.

As used herein, unless otherwise specified, the term "liquid aerosol" refers to a colloid in which the dispersed phase is a liquid and the dispersion medium is a gas. Examples of liquid aerosols as that term is used herein include but are not limited to clouds, condensation, fog, hair spray, and mist.

As used herein, unless otherwise specified, the term "sol" refers to a colloid in which the dispersed phase is a solid and the dispersion medium is a liquid. Examples of sols as that term is used herein include but are not limited to blood, pigmented ink, and the protein fraction of milk.

As used herein, unless otherwise specified, the term "solid aerosol" refers to a colloid in which the dispersed phase is a solid and the dispersion medium is a gas. Examples of solid aerosols as that term is used herein include but are not limited to atmospheric particulates, ice clouds, and smoke.

As used herein, unless otherwise specified, the term "solid foam" refers to a colloid in which the dispersed phase is a gas and the dispersion medium is a solid. Examples of solid foams as that term is used herein include but are not limited to aerogel, pumice, and Styrofoam.

As used herein, unless otherwise specified, the term "solid sol" refers to a colloid in which both the dispersed phase and the dispersion medium are solids. Examples of solid sols as that term is used herein include but are not limited to cranberry glass.

As used herein, unless otherwise specified, the term "stability" refers to the proportion of an initial volume of a foam that is retained by the foam after a specified interval. By way of non-limiting example, a foam that has an initial volume of five liters and a volume of four liters 14 days later thus has 80% stability over 14 days. Unless otherwise specified, a "stable" foam, as that term is used herein, is a foam that has at least 50% stability after a specified interval.

The present invention provides for rapid and prolific growth of filamentous fungi by culturing a filamentous fungus on or in an air-medium colloid (AMC), in which air is dispersed within a fermentation medium or growth medium. Typically, the AMC is provided with a stabilizer to improve the foam stability of the AMC and thus preserve the increased volume of the AMC over a longer period. In embodiments, the AMC is formed by aerating the fermentation medium, and may optionally include other components or features, e.g. polysaccharide amendments or a fungal inoculum, to provide even further improved fungal growth characteristics. Physically, the AMC is a generally stable, air-rich colloid, which in embodiments may be a foam.

Culturing of a filamentous fungus on or in an AMC may be employed in any of a wide variety of applications. As a first non-limiting example, use of an AMC may be included in a fermentation strategy for inoculation in a surface fermentation system or process. As a second non-limiting example, use of an AMC may be included in a fermentation strategy for inoculation in a solid substrate fermentation system or process. As a third non-limiting example, AMCs may be used in "membrane" fermentation systems, e.g. as disclosed and described in PCT Application Publication 2019/046480, or processes without a membrane; in these embodiments, the AMC itself may take the place of a membrane. As a fourth non-limiting example, AMCs may be used in fermentation "trays" or other similar vessels for the formation of biomats on a surface of the AMC and/or on an air/medium interface therein.

It is to be expressly understood that fungal biomass produced according to the methods and systems of the present invention may have any suitable geometry, and that a fermentation container, surface, or vessel may be selected to provide the AMC and/or the fungal biomass with the desired geometry. By way of non-limiting example, where fermentation is carried out on or within a container or surface, a biomat of the filamentous fungus may be produced. By way of further non-limiting example, the AMC may be sprayed, dip-coated, "painted," or otherwise coated on a surface of, a substrate or scaffold (e.g. a hydrophobic screen), whereby the fungal biomass may thus grow in a shape or pattern similar to a shape or pattern similar to that of the substrate or scaffold, and the shape of the substrate or scaffold may be preselected (e.g. cubical, spherical, etc.) to provide a corresponding desired fungal geometry.

The methods and systems of the present invention provide for more rapid and prolific growth of filamentous fungus than can be achieved by conventional methods and systems for culturing filamentous fungi. Without wishing to be bound by any particular theory, it is believed that, in embodiments, this benefit of the methods and systems of the present invention may be achieved as a result of the interaction of the AMC with hydrophobins produced by the filamentous fungus. Hydrophobins are small, cysteine-rich proteins that are naturally expressed by many species of filamentous fungi and self-assemble into a hydrophobic bilayer on hydrophilic/hydrophobic interfaces, such as a water/air interface. The fungus can then penetrate the hydrophilic/hydrophobic interface. In conventional surface fermentation, for instance, hydrophobins may form a bilayer on the interface between a liquid feedstock and the surrounding atmosphere, which is then penetrated by fungal tissues (which lie primarily on the air side of the interface) to reach the liquid feedstock. It is believed that, in the practice of the present invention, the AMC, which contains a significant volume fraction of air, greatly increases the effective surface area of the air/medium interface and thus the area over which hydrophobins may self-assemble and enable penetration of the fungus to reach the growth medium. Put another way, an AMC has a much greater effective surface area over which surface fermentation can take place than a conventional feedstock in a conventional surface fermentation process.

Methods and systems of the present invention are particularly suitable for the production of filamentous fungi as a source of food. Specifically, use of an AMC may enable the cultured filamentous fungus to grow much more rapidly and prolifically, without the need for growth enhancers or other additives that may negatively affect the safety, nutritional profile, or taste of the resulting fungus. At the same time, the AMC and/or the filamentous fungus may comprise food-grade or food-safe additives and ingredients; by way of non-limiting example, the AMC may comprise a food-grade or food-safe foam stabilizer, e.g. xanthan gum, which is not harmful if eaten and so does not pose a risk to consumers if absorbed by the fungus during fermentation. The nutritional profile, taste, or other characteristics of the filamentous fungus may also be enhanced or augmented by the inclusion of any one or more various food-grade or food-safe additives, such as (by way of non-limiting example) enrichment of the AMC with certain vitamins, minerals, or other nutrients.

As may be appreciated, various parameters of the AMC may be controlled or tuned to provide for a desired growth profile of the filamentous fungus. As a first non-limiting example, the relative quantity, distribution, bubble size, etc. of air dispersed within a volume of the fermentation medium may be selected to provide a desired foam structure, which may impact the growth of the filamentous fungus as described herein. As a second non-limiting example, a composition and amount of an optional foam stabilizer provided as part of the AMC may be selected to provide a desired foam stability profile over time. As a third non-limiting example, a composition and amount of an optional surfactant provided as part of the AMC may be selected to provide a desired surface tension or interfacial tension between any two of the air within the AMC, the liquid fermentation medium within the AMC, and the filamentous fungus; the use of a surfactant may also help to drive, define, and/or augment various other characteristics of the AMC, the filamentous fungus, and/or the fermentation process, including but not limited to a behavior of an inoculum of the filamentous fungus on or in air bubbles of the AMC, the energy associated with nucleating particles in the AMC, and/or a resultant foam size or volume. In general, then, any attribute or chemical or physical property of the AMC, and of colloids more generally, that can affect the surface behavior of the AMC and/or a filamentous fungus disposed therein or thereon may be controlled or tuned to provide for a desired growth profile of the filamentous fungus.

One chemical and/or physical characteristic of the AMC of interest in the methods and systems of the present invention is a surface activity of a foam stabilizer or surfactant present in the AMC. Specifically, a foam stabilizer or surfactant, if present, may be selected and provided in suitable quantities, based on a surface activity of the foam stabilizer or surfactant in the fermentation medium, to provide a desired surface tension of the AMC. Non-limiting examples of foam stabilizers and surfactants suitable for use in the invention include polysaccharide gums (e.g. xanthan gum, guar gum, locust bean gum, konjac root gum), anionic surfactants (e.g. carboxylates, phosphate esters, sulfate esters, sulfonate esters), cationic surfactants (e.g. primary, secondary, or tertiary amines, quaternary ammonium salts), ceteareth 20, cellulose, diacetyl tartaric esters of mono- and diglycerides (DATEM), diglycerides, emulsifying wax, glycerol monostearate, lecithins, monoglycerides, mustards, non-ionic surfactants (e.g. polysorbate 20, polysorbate 80), soaps, sodium phosphates, sodium stearoyl lactylate, zwitterionic surfactants, saponins, starches, modified starches, plant protein surfactants (e.g. soy protein isolate, pea protein isolate), animal protein surfactants (e.g. casein, whey protein isolate), microparticulates, silica, and combinations and mixtures thereof.

In the practice of the present invention, stabilizers and surfactants are generally present in an AMC in an amount of between about 0.1 wt % and about 2.5 wt %, or alternatively in any range from about any tenth of a percent by weight to about any other tenth of a percent by weight between 0.1 wt % and 2.5 wt %. By way of non-limiting example, stabilizers and surfactants may be present in an AMC in an amount of at least about 0.1 wt %, at least about 0.2 wt %, at least about 0.3 wt %, at least about 0.4 wt %, at least about 0.5 wt %, at least about 0.6 wt %, at least about 0.7 wt %, at least about 0.8 wt %, at least about 0.9 wt %, at least about 1.0 wt %, at least about 1.1 wt %, at least about 1.2 wt %, at least about 1.3 wt %, at least about 1.4 wt %, at least about 1.5 wt %, at least about 1.6 wt %, at least about 1.7 wt %, at least about 1.8 wt %, at least about 1.9 wt %, at least about 2.0 wt %, at least about 2.1 wt %, at least about 2.2 wt %, at least about 2.3 wt %, or least about 2.4 wt %. By way of further non-limiting example, stabilizers and surfactants may be present in an AMC in an amount of no more than about 2.5 wt %, no more than about 2.4 wt %, no more than about 2.3 wt %, no more than about 2.2 wt %, no more than about 2.1 wt %, no more than about 2.0 wt %, no more than about 1.9 wt %, no more than about 1.8 wt %, no more than about 1.7 wt %, no more than about 1.6 wt %, no more than about 1.5 wt %, no more than about 1.4 wt %, no more than about 1.3 wt %, no more than about 1.2 wt %, no more than about 1.1 wt %, no more than about 1.0 wt %, no more than about 0.9 wt %, no more than about 0.8 wt %, no more than about 0.7 wt %, no more than about 0.6 wt %, no more than about 0.5 wt %, no more than about 0.4 wt %, no more than about 0.3 wt %, or no more than about 0.2 wt %.

Another chemical and/or physical characteristic of the AMC of interest in the methods and systems of the present invention is a stability of the AMC when the AMC is provided as a foam. Although various assays are known and described in the literature for assessing the stability of a foam, the simplest methods for determining foam stability include simply measuring the height of an upper surface of the foam in the same vessel at two (or more) points in time. The stability of a foam may enable the foam to be stored and/or transported for a significant period after formulation, providing yet another advantageous benefit to the methods and systems of the present invention. In some embodiments when the AMC is a foam, it has a stability of at least about 50%, 60%, 70%, 80%, 90%, or 95% over 1 hour, 6 hours, 12 hours, 1 day, 2 days, 3 days, 4 days, 5 days, 6 days, 1 week or 2 weeks.

Still another chemical and/or physical characteristic of the AMC of interest in the methods and systems of the present invention is a texture of the AMC when the AMC is provided as a foam. Specifically, any one or more of the volume, cell structure, overrun, gas fraction, packing geometry, interfacial geometry, and other similar features of the foam may be selected and/or designed to provide a desired effect on the growth of the filamentous fungus, as may be various properties of the dispersion medium, such as water activity, ionic strength, osmotic pressure, and the like. In particular, these and other features of foamed AMCs may affect the effective surface area of the AMC available for fermentation, which as described throughout this disclosure has a significant impact on the resulting yield of filamentous fungus.

Yet another chemical and/or physical characteristic of the AMC of interest in the methods and systems of the present invention is a relationship between the viscosity and the stability of the AMC when the AMC is provided as a foam. In many applications, such as when process operations require the AMC to be poured, pumped, stored, and/or transported, it may generally be desirable to increase the stability of the foamed AMC without increasing the AMC's viscosity. The selection of a desired stability and a desired viscosity may, in turn, affect the selection and/or amount of a provided foam stabilizer, surfactant, thickener, etc.

Yet another chemical and/or physical characteristic of the AMC of interest in the methods and systems of the present invention is a molar carbon-to-nitrogen ratio in the fermentation medium. By way of non-limiting example, a molar carbon-to-nitrogen ratio in the fermentation medium may be at least about 10, at least about 11, at least about 12, at least about 13, at least about 14, at least about 15, at least about 16, at least about 17, at least about 18, at least about 19, at least about 20, at least about 21, at least about 22, at least about 23, at least about 24, or at least about 25, or between about 10 and about 25, or in a range between about any whole number and about any other whole number between 10 and 25. In some embodiments, a molar carbon-to-nitrogen ratio in the fermentation medium may preferably be between about 12 and about 20.

The AMCs of the present invention may be aerated, or otherwise have air or any other gas dispersed therein, by any suitable means, at aeration rates and for times selected to provide a desired air fraction and/or foam stability to the AMC. By way of first non-limiting example, where the volume of fermentation medium used to form the AMC is relatively small, an immersion blender or similar device may be used; typical household immersion blenders generally comprise two or more blades which rotate at high speeds (at least about 12,000 rpm) and are therefore well-adapted to aerate a liquid fermentation medium. By way of second non-limiting example, an AMC in the form of a foam may be generated by aerating a liquid growth medium with a static mixing head, and/or by whipping the liquid growth medium using a whisk, stand mixer, or the like. By way of third non-limiting example, where the volume of fermentation medium used to form the AMC is larger or where more precision over the aeration is desired, industrial aeration equipment, such as a high-volume and/or high-shear mixer, with or without an air bubbler, or the application of an applied positive or negative pressure, may be used. Other devices, methods, and systems for forming the AMC, such as the use of static and dynamic mixing heads, bubbling, a scrape-side heat exchanger, extrusion, pressure differential methods, and so on are expressly contemplated and are within the scope of the present invention. Control over the aeration may be desirable for various reasons, including but not limited to providing the AMC with a desired air cell size; without wishing to be bound by any particular theory, it is believed that there is a positive correlation between air cell size and viscosity (i.e. smaller air cells result in lower viscosity, larger air cells result in higher viscosity) and a negative correlation between air cell size and foam stability (i.e. smaller air cells result in higher foam stability, larger air cells result in lower foam stability).

In the practice of the present invention, inoculation and culturing of the filamentous fungus on or in the AMC may take place in any suitable fermentation vessel. Generally, a height, cross-sectional area, and/or volume of the fermentation vessel may be selected to provide a desired effect on the AMC and/or the fermentation process. By way of non-limiting example, and without wishing to be bound by any particular theory, it may be that, ceteris paribus, a greater volume of AMC results in greater foam stability (or, equivalently, a slower rate of loss of volume or "drainage" of the foam); this may be the result of capillary action working against gravity to maintain the keep the AMC in a foamed state. Foam stability may also be dependent on a drainage or disproportionation rate of the foam, which may be driven by stability of the interfacial surfaces of the colloid and a Laplace pressure differential (bubble size and size distribution).

In embodiments in which the AMC is provided in the form of a foam, the internal physical structure of the foam, i.e. the arrangement of air cells and the network of liquid films separating the air cells may be thought of as a "scaffold" on which biomass or portions of biomass may adhere and grow. Thus, the structure of this "scaffold" may, in some embodiments, be a particularly important consideration, and the size of the air cells or bubbles within the foam, together with other foam parameters, may be selected to provide a desired scaffold structure. Characteristics of the aeration process used to form the AMC from the fermentation medium may be tuned with these or other foam characteristics in mind, particularly to provide a desired growth pattern, profile, or rate, e.g. a preselected doubling rate of an area or mass of the fungal biomass produced by the culturing methods of the present invention.

Electrostatic and/or ionic forces on a surface or within a volume of the AMC may also provide a significant effect on the suitability of the AMC for a desired application or the growth of the cultured filamentous fungus. As a first non-limiting example, certain properties of a foamed AMC, including but not limited to a thickness of the foam, may depend, at least in part, on a pH of the AMC and/or foam stabilizers or thickeners contained therein. As a second non-limiting example, an electrostatic disjoining pressure of the film may impact a balance between forces on the surface of the foam and the capillary forces drawing the liquid fermentation medium upward, and thus the formation and composition of certain types of film on the surface of the foam. As a third non-limiting example, electrochemical interactions at the air/foam interface may promote or inhibit fungal growth or adhesion. As a fourth non-limiting example, the isoelectric point of a foam stabilizer or surfactant used in the AMC may have additional chemical and/or physical effects on the AMC and/or the filamentous fungus.

Applications for AMCs

It is to be expressly understood that AMCs according to the present invention may suitably be utilized in conjunction with known methods and systems for culturing filamentous fungi. By way of non-limiting example, an AMC may be used as the feedstock in a membrane fermentation process and/or in a "bioreactor." Additionally and/or alternatively, AMCs may be used in any suitable fermentation vessel, including but not limited to fabrics, membranes, mesh screens, plates, trays, vats, and other vessels. In particular, mesh screens having pore diameters of up to about 0.25 millimeters, up to about 0.5 millimeters, up to about 0.75 millimeters, up to about 1 millimeter, up to about 1.25 millimeters, up to about 1.5 millimeters, up to about 1.75 millimeters, up to about 2 millimeters, up to about 3 millimeters, up to about 4 millimeters, up to about 5 millimeters, up to about 6 millimeters, up to about 7 millimeters, up to about 8 millimeters, up to about 9 millimeters, or up to about 10 millimeters can suitably have AMCs applied thereto in the practice of embodiments of the present invention.

One advantage of the AMCs of the present invention is that they may be provided with a viscosity suitable to allow them to be "painted" or otherwise coated onto a surface of a substrate or scaffold, and so do not need to be provided in a vessel having an internal cavity for holding the AMC. In fact, the present inventors have successfully coated vertically disposed mesh screens with AMCs and cultured filamentous fungus thereon, thus providing not only a desired shape but also a desired spatial orientation of fungal growth. High-viscosity AMCs of the present invention may, in some embodiments, take the form of, e.g., a spray foam that may be applied to a desired incubation surface by a user.

Reactors and vessels used in conjunction with AMCs of the present invention may be designed to provide certain predefined physical parameters for the AMC and thus for the culturing or fermentation process. Such physical parameters include but are not limited to the physical parameters described throughout this disclosure.

One advantageous application for the methods and systems of the present invention is for the production of filamentous fungus biomass that may be used as a foodstuff, as a structural material, or as a textile, by way of non-limiting example. In addition, methods and systems of the present invention can be for production of desirable metabolic products of a filamentous fungus. By way of non-limiting example, methods and systems of culturing a filamentous fungus on or in an AMC according to the present invention may be exploited to stimulate production of any one or more of an organic acid, an antibiotic, an enzyme, a hormone, a lipid, a mycotoxin, a vitamin, a pigment, and a recombinant heterologous protein by the filamentous fungus. Among common filamentous fungus metabolites that may be particularly desirable to synthesize by these methods is gibberellic acid, which has a number of important horticultural uses, including but not limited to use a germination stimulant, a production-boosting hormone in grape-growing, a growth replicator in cherries, and a supplement to citrus fruit crops that promotes the growth of seedless fruit. Metabolites produced by filamentous fungi cultured according to the present invention may include both growth-associated metabolites and non-growth-associated metabolites. In some embodiments, production of a desired metabolite may optionally be stimulated by milling a solid substrate and adding the milled solid substrate to the AMC prior to or during fermentation.

Biomats produced by the methods and systems disclosed herein may be useful in a wide variety of applications. By way of first non-limiting example, biomats produced according to the present invention may be transformed into foodstuffs by any one or more methods known to those skilled in the art, for example as disclosed in PCT Application Publications 2019/046480 and 2020/176758. In general, biomats produced according to the present invention may be incorporated into foodstuffs in the form of large particles or filaments (e.g. to make a meat analog food product), fine particles (e.g. to make a flour), a liquid dispersion of particles (e.g. to make a milk analog food product), or any other suitable form. Foodstuffs made from filamentous fungal biomats produced according to the methods and systems disclosed herein, which are subsequently transformed into the foodstuff by any one or more known methods and systems, are therefore within the scope of the present disclosure.

By way of second non-limiting example, biomats produced according to the present invention may be transformed into structural materials, such as building materials, by any one or more methods known to those skilled in the art, for example as disclosed in U.S. Pat. Nos. 9,555,395 and 9,951,307. In general, biomats produced according to the present invention may be incorporated into structural materials by being combined with a lignocellulosic material or growth medium, or by any other suitable means. Structural materials made from filamentous fungal biomats produced according to the methods and systems disclosed herein, which are subsequently transformed into the structural material by any one or more known methods and systems, are therefore within the scope of the present disclosure.

By way of third non-limiting example, biomats produced according to the present invention may be transformed into textiles, such as leather analog textiles, by any one or more suitable methods. Most typically, such methods may include causing a solution of a polymer and/or crosslinker to infiltrate the biomat (which may optionally be previously, simultaneously, or subsequently size-reduced) and then curing the biomat to remove the solvent, but in the most general sense, biomats produced according to the present invention may be transformed into textiles by any suitable method of modifying chemical or physical properties of the biomat (e.g. by crosslinking, combining with a polymer or other structural reinforcing material, etc.) to provide a desired material or mechanical property. Textiles made from filamentous fungal biomats produced according to the methods and systems disclosed herein, which are subsequently transformed into the textile by any one or more suitable methods and systems, are therefore within the scope of the present disclosure.

Growth and Microstructure of Fungal Biomass

In the practice of the methods of the present invention, fungal biomass may be produced that has a desired growth characteristic, which in many cases will correspond to a desired chemical or physical structure, in particular a physical microstructure, of the fungal biomass. By way of first non-limiting example, a biomass that has a desired spatial distribution of AMC constituents throughout the biomass may be produced by the methods disclosed herein. By way of second non-limiting example, a desired spatial distribution of a fungal inoculum throughout the AMC may be achieved by the methods disclosed herein (which may, in turn, result in production of a biomass having a desired physical characteristic). By way of third non-limiting example, a desired pattern of mycelial network nucleation and/or development may be achieved by the methods disclosed herein, particularly by modification or tuning of particular AMC and/or inoculum characteristics. By way of fourth non-limiting example, a biomass having a spatially varying physical composition, e.g. having spatial variations in the concentration of particular fungal tissues, may be produced by the methods disclosed herein. By way of fifth non-limiting example, a biomass having a spatially varying chemical composition or behavior, e.g. having spatial variations in respiration rate, protein content, nutrient (e.g. carbon or nitrogen) utilization, and the like, may be produced by the methods disclosed herein. By way of sixth non-limiting example, a biomass having a desired metabolic characteristic, e.g. a preselected metabolic efficiency, increased or decreased production of a selected metabolite, etc., may be produced by the methods disclosed herein. By way of seventh non-limiting example, a biomass having a desired carbon dioxide production rate or profile may be produced by the methods disclosed herein. By way of eighth non-limiting example, production of a biomass may be effectively segregated into distinct stages, e.g. initial nucleation, combination of nucleation sites, evolution of a thin cohesive film, vertical growth of the biomass, evolution and growth of distinct layers of biomass, etc., by the methods disclosed herein (which may, in turn, result in production of a biomass having a desired physical characteristic). By way of ninth non-limiting example, a biomass having a desired characteristic relevant to a consumer of the filamentous fungus as a food product, e.g. biomass (dry) density, conversion efficiency, nutrient profile, taste, visual appearance, aroma, protein binding, mycotoxin content, etc., may be produced by the methods disclosed herein; in some embodiments, a dry density of the biomat may be at least about $0.19 \text{ g/cm}^3$, at least about $0.20 \text{ g/cm}^3$, at least about $0.21 \text{ g/cm}^3$, or at least about $0.22 \text{ g/cm}^3$. By way of tenth non-limiting example, a biomass having a desired wet density may be produced by the methods disclosed herein, which may improve the suitability of the biomass for use in a desired application (e.g. as food, as a textile material, etc.) and/or improve the ease with which the biomass may be subsequently processed.

In some embodiments, particularly those in which the AMC is provided in the form of a foam, cells of the filamentous fungus may remain preferentially sequestered in the foam after harvesting of the biomats, with filaments of fungus adhered to the surface of bubbles within the foamed AMC. This may be advantageous or desirable in applications in which, for example, the AMC may be subsequently processed to obtain further biomass from the surface of bubbles within the AMC.

In some embodiments, growth of a filamentous fungal biomat on an AMC may result in a biomat having a decreased or minimized content of microconidia and/or an increased or maximized content of fungal hyphae. By way of non-limiting example, microconidia may make up less than about 50%, less than about 40%, less than about 30%, less than about 20%, less than about 10%, less than about 5%, less than about 4%, less than about 3%, or less than about 2% of a filamentous fungal biomat produced according to the present invention. By way of further non-limiting example, fungal hyphae may make up at least about 50%, at least about 60%, at least about 70%, at least about 80%, at least about 90%, at least about 95%, at least about 96%, at least about 97%, or at least about 98% of a filamentous fungal biomat produced according to the present invention. Without wishing to be bound by any particular theory, it is believed that filamentous fungal biomats having an increased or maximized content of fungal hyphae may be particularly useful or suitable for certain application, e.g. in textile materials, due to material or mechanical properties resulting from this increased or maximized hyphal content, e.g. increased tensile strength.

Rheology and Structure of AMC Foams

The methods and systems of the invention described herein may be used to produce AMCs having desired physical and mechanical properties, and particularly to produce AMC foams having desired rheologies and related characteristics. By way of first non-limiting example, properties of the air cells dispersed throughout the AMC, e.g. void fraction, bubble size, bubble size distribution, bubble shape, and bubble surface area, may be characterized and controlled according to the present invention. By way of second non-limiting example, degradation properties of the AMC, e.g. foam stability as a function of time, chemical degradation pathways of the foam, and physical interactions with a fungal inoculum as a function of time, may be characterized and controlled according to the present invention, particularly by use of varying AMC chemistries and fungal inoculum species and loading rates. As a third non-limiting example, fluid properties of the AMC, e.g. viscosity, rheology, power law or Bingham plastic behavior, may be characterized and controlled according to the present invention, particularly by controlling the gas fraction of the AMC. By way of fourth non-limiting example, working properties of the AMC, e.g. shear thinning or shear thickening properties, may be characterized and controlled according to the present invention. By way of fifth non-limiting example, changes in chemical or physical behavior of the AMC over time may be characterized and controlled according to the present invention, particularly by varying a loading rate of the fungal inoculum. By way of sixth non-limiting example, effects of foam stabilizers and surfactants, e.g. hydrophobins and xanthan gum, may be characterized and controlled according to the present invention. By way of seventh non-limiting example, effects of other additives, e.g. nutrient supplements, may be characterized and controlled according to the present invention. By way of eighth non-limiting example, the effect of foam formation mechanism, e.g. static packing, rotor/stator formation, and air induction, may be characterized and controlled according to the present invention.

Other Process Considerations, Advantages, and Benefits

In many embodiments, it may be desirable to include a foaming agent, foam stabilizer, surfactant, or the like in AMCs of the present invention. As described throughout this disclosure, xanthan gum is a very commonly used foam stabilizer and is safe for use in food-grade applications. However, many other gums, foaming agents, foam stabilizers, surfactants, thickeners, and so on are known and described in the art, and may suitably be used in the practice of the present invention. These additives may, in embodiments, have differing effects on the stability and other parameters of the AMC and may be selected for suitability in a particular application. Examples of foaming agents, foam stabilizers, and/or surfactants that may suitably be used in the practice of the present invention include but are not limited to anionic surfactants (e.g. carboxylates, phosphate esters, sulfate esters, sulfonate esters), cationic surfactants (e.g. primary, secondary, or tertiary amines, quaternary ammonium salts), ceteareth 20, cellulose, diacetyl tartaric esters of mono- and diglycerides (DATEM), diglycerides, emulsifying wax, lecithins, monoglycerides, mustards, nonionic surfactants (e.g. amine oxides, ethoxylates, fatty acid esters of polyhydroxy compounds, phosphine oxides, sulfoxides), polysorbate 20, soaps, sodium phosphates, sodium stearoyl lactylate, zwitterionic surfactants, saponins, starches, modified starches, and protein isolates from both plant and animal sources.

In embodiments, two or more stabilizers, surfactants, thickeners, etc. may be provided, and in some cases may have a synergistic effect on foam stability that is greater than simple additive extrapolation of their separate effects would predict. Particularly, when xanthan gum is used in combination with a galactomannan (e.g. guar gum, locust bean gum) and/or glucomannan (e.g. konjac gum) polymer, the present inventors have found that stable foams may be produced at xanthan addition rates of as little as 0.025 wt % of the fermentation medium. AMCs of these embodiments may exhibit both shear thinning (e.g. lower viscosity at higher shear rate) and heat thinning (e.g. lower viscosity at higher temperature), which may be desirable in certain applications of the present invention.

The chemical composition of the fermentation medium may itself be selected to achieve a desired growth rate, composition, etc. of the fungal biomass. In particular, the identity of the carbon source, e.g. fructose, in the fermentation medium may have a significant impact on such outcomes as growth profile, carbon utilization rate, and the like.

The fermentation medium may, in embodiments, be or comprise a feedstock comprising a carbon source and a nitrogen source, and particularly may be or comprise a feedstock suitable for use in a bioreactor fermentation process. Suitable carbon sources are sugars (e.g. sucrose, maltose, glucose, fructose, Japan rare sugars, etc.), sugar alcohols (e.g. glycerol, polyol, etc.), starch (e.g. corn starch, etc.), starch derivative (e.g. maltodextrin, cyclodextrin, glucose syrup, hydrolysates and modified starch), starch hydrolysates, hydrogenated starch hydrolysates (HSH; e.g. hydrogenated glucose syrups, maltitol syrups, sorbitol syrups, etc.), lignocellulosic pulp or feedstock (e.g. sugar beet pulp, agricultural pulp, lumber pulp, distiller dry grains, brewery waste, etc.), corn steep liquors, acid whey, sweet whey, milk serum, wheat steep liquors, carbohydrates, food waste, olive oil processing waste, hydrolysate from lignocellulosic materials, corn wet milling produces (e.g. carbon refined syrups, demineralized syrups, enzyme converted syrups, etc.) and/or combinations thereof. The feedstock can be a waste product, such as naturally occurring urine and/or feces, food waste, plant material, industrial waste such as glycerol, and waste by-products, starch and/or by products of starch hydrolysis, acid whey, sugar alcohol, and/or combinations thereof. Synthesized or manufactured waste surrogates, such as surrogate human urine can also be used. Plant material feedstocks are typically lignocellulosic. Some examples of lignocellulosic feedstock are agricultural crop residues (e.g. wheat straw, barley straw, rice straw, small grain straw, corn stover, corn fibers (e.g. corn fiber gum (CFG), distillers dried grains (DDG), corn gluten mean (CGM), switch grass, sugar beet pulp, waste streams from palm oil production, hay-alfalfa, sugarcane bagasse, non-agricultural biomass (e.g. algal biomass, cyanobacterial biomass, urban tree residue), forest products and industry residues (e.g., softwood first/secondary mill residue, hard softwood first/secondary mill residue, recycled paper pulp sludge), lignocellulosic containing waste (e.g. newsprint, waste paper, brewing grains, used rubber tire (URT), municipal organic waste and by-products, yard waste and by-products, clinical organic waste and by-products, and waste and by-products generated during the production of biofuels (e.g. processed algal biomass, glycerol), and combinations thereof.

The AMC may, optionally, further comprise one or more salts. In many fungal culturing and fermentation processes, salts such as ammonium nitrate are often used to boost the metabolic activity and/or growth rate of the fungus. These and other salts may be used for similar purposes in the AMCs of the present invention.

The AMC may, optionally, further comprise one or more other food-grade additives. These additives may be provided for any of several purposes, from modifying the physical behavior of the colloid to modifying a taste or nutritional content of the resulting biomass.

Generally, any filamentous fungus suitable for culture and fermentation in the methods and systems of the prior art may likewise be used in the practice of the present invention. Such fungi include, but are not limited to, *Fusarium vene-*

*natum*, Morel mushrooms, pearl mushrooms, and other mushrooms suitable for consumption as food by humans. More generally, the filamentous fungus may belong to an order selected from the group consisting of *Ustilaginales, Russulales, Polyporales, Agaricales, Pezizales*, and *Hypocreales*; may belong to a family selected from the group consisting of *Ustilaginaceae, Hericiaceae, Polyporaceae, Grifolaceae, Lyophyllaceae, Strophariaceae, Lycoperdaceae, Agaricaceae, Pleurotaceae, Physalacriaceae, Omphalotaceae, Tuberaceae, Morchellaceae, Sparassidaceae, Nectriaceae*, and *Cordycipitaceae*; and/or may belong to a species selected from the group consisting of *Ustilago esculenta, Hericulum erinaceus, Polyporous squamosus, Grifola fondosa, Hypsizygus marmoreus, Hypsizygus ulmarius, Calocybe gambosa, Pholiota nameko, Calvatia gigantea, Agaricus bisporus, Stropharia rugosoannulata, Hypholoma lateritium, Pleurotus eryngii, Pleurotus ostreatus, Tuber borchii, Morchella esculenta, Morchella conica, Morchella importuna, Sparassis crispa, Fusarium venenatum*, MK7 ATCC Accession Deposit No. PTA-10698, *Disciotis venosa*, and *Cordyceps militaris*. It is to be specifically appreciated that an inoculum of a fungus may behave identically when cultured in or on an AMC relative to a conventional growth medium, or the inoculum may have additional or alternative advantageous or beneficial behavior characteristics when cultured in or on an AMC relative to a conventional growth medium; these characteristics include, but are not necessarily limited to, aggregation behavior, growth pattern or rate, and so on. The spatial distribution of the inoculum on the growth surface may likewise be selected to provide a desired effect on fungal growth pattern, AMC foam morphology or structure, and so on.

In embodiments, the AMC may be provided as a layer or coating on another growth surface. Such additional and/or alternative growth surfaces include, but are not necessarily limited to, a solid surface, a synthetic mesh, a lignocellulosic material such as cotton, and the like.

As described throughout this disclosure, electrochemical properties of the AMC may be modified, selected, and/or tuned to improve or control a growth profile of the filamentous fungus. Examples of electrochemical properties of the AMC that may be modified, selected, and/or tuned according to the present invention include electrical conductivity and zeta potential.

In the practice of the present invention, AMCs, once produced, may or may not be actively aerated during fermentation of the filamentous fungus. Decisions as to whether and under what conditions to actively aerate the AMC during fermentation can, in embodiments, be driven by equipment and resource availability and desired characteristics of the biomass to be produced, among other considerations. Likewise, foam stabilizers (e.g. xanthan gum), surfactants, and other additives may or may not be used in AMCs of the present invention, depending on these and other considerations.

An important consideration in the practice of the present invention is the manner and rate of air transfer to, across and/or through the fermentation surface. Specifically, by culturing filamentous fungus in or on an AMC, the present invention increases the effective surface area available for active fermentation. Fermentation may thus be carried out, for example, on the surface of air bubbles, cells, or pockets within the AMC; stated slightly differently, where previous fermentation processes have generally limited the fermentation to a "2D" or planar region (i.e. the air/medium interface or surface), the present invention allows for "3D" fermentation of a much greater portion of the spatial extent or volume of the fermentation medium. Effectively, then, the present invention improves upon natural fungal growth processes, without the need for shear or active aeration, particularly when accounting for air diffusion through air bubbles, cells, or pockets dispersed throughout the AMC. The resulting 3D structure and porosity of the fungal network may, in embodiments, allow for an increased or tuned gas diffusion rate or gas permeation rate through the fungal network.

The methods and systems of the present invention have various advantages and benefits relative to previous methods and systems for the production of filamentous fungus biomass. A first non-limiting advantage and/or benefit of the present invention is that active aeration or agitation of the liquid fermentation medium is not needed subsequent to the initial formation of the AMC; in particular, where other fermentation processes are generally aerobic processes that rely primarily on passive (rather than active) oxygen transfer, the present invention increases an air-to-medium ratio in a more stable and controllable manner and thus permits precise regulation of air exchange. A second non-limiting advantage and/or benefit of the present invention is in situ aggregation of fungal biomass into a single coherent mat, such that the mat has significant tensile strength to allow for easy harvesting. A third non-limiting advantage and/or benefit of the present invention is that the methods and systems of the invention are effective to produce textured biomass, which can be used in a wide variety of products, e.g. food, bioplastics, biofuels, nutritional supplements, and expression platforms for a variety of pharmaceuticals. A fourth non-limiting advantage and/or benefit of the present invention is a significant reduction in water consumption and other residual waste products per kilogram of biomass produced, particularly regarding waste of the fermentation medium itself. A fifth non-limiting advantage and/or benefit of the present invention is more rapid biomass production; a cohesive biomat can, according to the present invention, be produced in as little as eighteen hours. A sixth non-limiting advantage and/or benefit of the present invention is increased biomass density in a biomat. A seventh non-limiting advantage and/or benefit of the present invention is that the methods and systems of the invention may be employed to produce biomass of any of a wide variety of filamentous fungi, including extremophiles, allowing selection of a filamentous fungus having specific advantages for a desired application. An eighth non-limiting advantage and/or benefit of the present invention is improved scalability, allowing for production capacities and rates to be straightforwardly adjusted or modified without affecting the productivity of the methods and systems of the invention. A ninth non-limiting advantage and/or benefit of the present invention is the ability to utilize a wide variety of carbon- and/or nitrogen-rich substrates, including those produced during space missions or natural disasters, as a productive fermentation medium for the culture and production of filamentous fungi.

In some embodiments, methods of the present invention may produce an "area yield," defined herein as a mass of biomat per top surface area of the AMC on which the biomat is grown, of at least about 0.5 kg/m$^2$, at least about 0.6 kg/m$^2$, at least about 0.7 kg/m$^2$, at least about 0.8 kg/m$^2$, at least about 0.9 kg/m$^2$, at least about 1.0 kg/m$^2$, at least about 1.1 kg/m$^2$, at least about 1.2 kg/m$^2$, at least about 1.3 kg/m$^2$, at least about 1.4 kg/m$^2$, at least about 1.5 kg/m$^2$, at least about 1.6 kg/m$^2$, at least about 1.7 kg/m$^2$, at least about 1.8 kg/m$^2$, at least about 1.9 kg/m$^2$, or at least about 2.0 kg/m$^2$. In particular embodiments, such yields may be achieved when stabilizers are used in amounts of at least about 0.1 wt %, at least about 0.2 wt %, at least about 0.3 wt %, at least about 0.4 wt %, at least about 0.5 wt %, or at least about 0.6 wt %, and particularly when the stabilizer comprises xanthan gum. In particular embodiments, such yields may be achieved when a molar carbon-to-nitrogen ratio in the fermentation medium is between about 10 and about 23, or between about 11 and about 22, or between about 12 and 21, or between about 13 and about 20, or between about 14 and about 19, or between about 15 and about 18, or between about 16 and about 17. In particular embodiments, such yields may be achieved when a viscosity of the AMC is no more than about 12,000 cP, or no more than about 11,000 cP, or no more than about 10,000 cP, or no more than about 9,000 cP, or no more than about 8,000 cP, or no more than about 7,000 cP.

In some embodiments, methods of the present invention may produce a biomat having a dry mass density of at least about 0.15 g/cm$^3$, at least about 0.16 g/cm$^3$, at least about 0.17 g/cm$^3$, at least about 0.18 g/cm$^3$, at least about 0.19 g/cm$^3$, at least about 0.20 g/cm$^3$, at least about 0.21 g/cm$^3$, or at least about 0.22 g/cm$^3$. In particular embodiments, such densities may be achieved when stabilizers are used in amounts of at least about 0.1 wt %, at least about 0.2 wt %, at least about 0.3 wt %, at least about 0.4 wt %, at least about 0.5 wt %, or at least about 0.6 wt %, and particularly when the stabilizer comprises xanthan gum. In particular embodiments, such densities may be achieved when a molar carbon-to-nitrogen ratio in the fermentation medium is between about 10 and about 23, or between about 11 and about 22, or between about 12 and 21, or between about 13 and about 20, or between about 14 and about 19, or between about 15 and about 18, or between about 16 and about 17. In particular embodiments, such densities may be achieved when a viscosity of the AMC is no more than about 12,000 cP, or no more than about 11,000 cP, or no more than about 10,000 cP, or no more than about 9,000 cP, or no more than about 8,000 cP, or no more than about 7,000 cP.

In some embodiments, methods of the present invention may produce a biomat having a tensile strength, either before or after being boiled, of at least about 255 kPa, at least about 260 kPa, at least about 265 kPa, at least about 270 kPa, at least about 275 kPa, at least about 280 kPa, at least about 285 kPa, at least about 290 kPa, at least about 295 kPa, or at least about 300 kPa. In particular embodiments, such tensile strengths may be achieved when stabilizers are used in amounts of at least about 0.1 wt %, at least about 0.2 wt %, at least about 0.3 wt %, at least about 0.4 wt %, at least about 0.5 wt %, or at least about 0.6 wt %, and particularly when the stabilizer comprises xanthan gum. In particular embodiments, such tensile strengths may be achieved when a molar carbon-to-nitrogen ratio in the fermentation medium is between about 10 and about 23, or between about 11 and about 22, or between about 12 and 21, or between about 13 and about 20, or between about 14 and about 19, or between about 15 and about 18, or between about 16 and about 17. In particular embodiments, such tensile strengths may be achieved when a viscosity of the AMC is no more than about 12,000 cP, or no more than about 11,000 cP, or no more than about 10,000 cP, or no more than about 9,000 cP, or no more than about 8,000 cP, or no more than about 7,000 cP.

In some embodiments, methods of the present invention may produce a biomat having a thickness of at least about 1.75 mm, at least about 1.80 mm, at least about 1.85 mm, at least about 1.90 mm, at least about 1.95 mm, at least about 2.00 mm, at least about 2.05 mm, at least about 2.10 mm, at least about 2.15 mm, at least about 2.20 mm, at least about 2.25 mm, or at least about 2.30 mm. In particular embodiments, such thicknesses may be achieved when stabilizers are used in amounts of at least about 0.1 wt %, at least about 0.2 wt %, at least about 0.3 wt %, at least about 0.4 wt %, at least about 0.5 wt %, or at least about 0.6 wt %, and particularly when the stabilizer comprises xanthan gum. In particular embodiments, such thicknesses may be achieved when a molar carbon-to-nitrogen ratio in the fermentation medium is between about 10 and about 23, or between about 11 and about 22, or between about 12 and 21, or between about 13 and about 20, or between about 14 and about 19, or between about 15 and about 18, or between about 16 and about 17. In particular embodiments, such thicknesses may be achieved when a viscosity of the AMC is no more than about 12,000 cP, or no more than about 11,000 cP, or no more than about 10,000 cP, or no more than about 9,000 cP, or no more than about 8,000 cP, or no more than about 7,000 cP.

It is to be expressly understood that although the present invention has generally been described as utilizing colloids of air in a liquid fermentation medium, any gas suitable for use in a fungal culture or growth process may be dispersed in a foam in addition to or instead of air. Indeed, the gas to be dispersed in the foam may, in embodiments, be selected to achieve, by way of non-limiting example, a chemical or physical composition of the resulting fungal biomass that cannot be achieved using air.

The invention is further described with reference to the following illustrative, non-limiting Examples.

Example 1

This Example illustrates the use of a foam stabilizer in an AMC of the present invention and demonstrates that significantly improved yields of biomass and reduced tray waste can be achieved by use of a foam stabilizer.

Six AMCs were prepared by aerating a volume of standard inoculated MK102 fermentation medium, the composition of which (on a basis of nine liters of total medium) is defined in Table 1, with a typical household immersion blender (12000 rpm) for 15 seconds and pouring 200 mL of the aerated fermentation medium into a glass tray having a surface area of 0.02 m$^2$. Four of the six prepared AMCs contained up to 0.4 wt % food-grade xanthan gum as a stabilizer.

TABLE 1

| Ingredient | Amount |
| --- | --- |
| Ammonium nitrate | 91.329 g |
| Urea | 30.805 g |
| Calcium chloride dihydrate | 11.922 g |
| Magnesium sulfate heptahydrate | 9.000 g |
| Monopotassium phosphate | 36.000 g |
| Trace EDTA | 3.600 mL |
| Glycerol | 0.900 kg |
| Yeast extract | 13.500 g |
| Water | 8.286 L |
| Concentrated hydrogen chloride (to adjust pH to 2.7) | 7.3 mL |

All AMCs were observed to be pourable, self-leveling, and sufficiently inviscid to be pumped using standard equipment. AMCs comprising 0.1 wt % xanthan gum or less did not form stable foams, while AMCs comprising more than 0.1 wt % xanthan gum formed substantially homogeneous foams that remained stable for the duration of the experiment. It was also observed that the AMCs containing xanthan gum exhibited both continuous phase gelation and shear thinning, behaving as fluids when stirred or pumped but as a gel when at rest.

An inoculum of MK7 ATCC Accession Deposit No. PTA-10698 was introduced onto the surface of each AMC, and the six trays containing the AMCs were placed in an incubator and cultured for four days. After the four-day culture period, biomats of the filamentous fungus were harvested and processed by steaming (to inactivate the fungus) and pressing (to remove water). Various parameters of the mats were measured; the results are given in Table 2.

TABLE 2

| Sample # | Xanthan wt % | Pre-processing mass (g) | Post-processing mass (g) | Solids % | Yield (kg/m$^2$) |
|---|---|---|---|---|---|
| 1 | 0 | 25.096 | 10.503 | 24 | 0.52 |
| 2 | 0 | 21.315 | 10.416 | 23 | 0.52 |
| 3 | 0.1 | 31.721 | 10.391 | 24 | 0.52 |
| 4 | 0.2 | 64.233 | 38.480 | 18 | 1.9 |
| 5 | 0.3 | 51.993 | 34.011 | 25 | 1.7 |
| 6 | 0.4 | 51.500 | 28.100 | 26 | 1.4 |

All biomats had acceptable coloration, odor, and tensile strength.

FIG. 1 is an image of the biomats obtained (from left to right, top to bottom: Sample #6, Sample #3, Sample #1, Sample #2, Sample #5, Sample #4). As illustrated in Table 1 and FIG. 1, AMCs in the form of stable foams produced significantly enhanced yields of biomat relative to unstable foams.

Figure 2:
FIG. 2 illustrates two trays in which filamentous fungus was grown on an AMC, according to embodiments of the present invention, and one tray in which filamentous fungus was grown on a standard non-emulsified growth medium.

FIG. 2 is an image of the trays in which a control sample (top), Sample #4 (bottom left), and Sample #5 (bottom right) were cultured. As illustrated in FIG. 2, the proportion of fermentation medium remaining in the tray after fermentation, i.e. "tray waste," is greatly reduced for samples grown on stable foam AMCs. This is consistent with the hypothesis that stable AMCs provide a greater effective surface area for fermentation and therefore readier availability of the fermentation medium to the filamentous fungus. Without wishing to be bound by any particular theory, it is believed that this greater effective surface area reduces tray waste by allowing the filamentous fungus to convert a greater proportion of the nutrients in the growth medium into biomass, increasing the biomat. Photomicrographs (not illustrated) of the AMCs appeared to indicate that fungal cells remained preferentially sequestered in the foam after harvesting of the biomats, with filaments of fungus adhered to the surface of bubbles within the foamed AMCs.

Example 2

This Example illustrates a comparison between growth of a filamentous fungus on an AMC and growth of a filamentous fungus in a conventional surface fermentation process and demonstrates that significantly accelerated growth, and significantly improved yields, of biomass can be achieved by use of an AMC.

Figure 3:
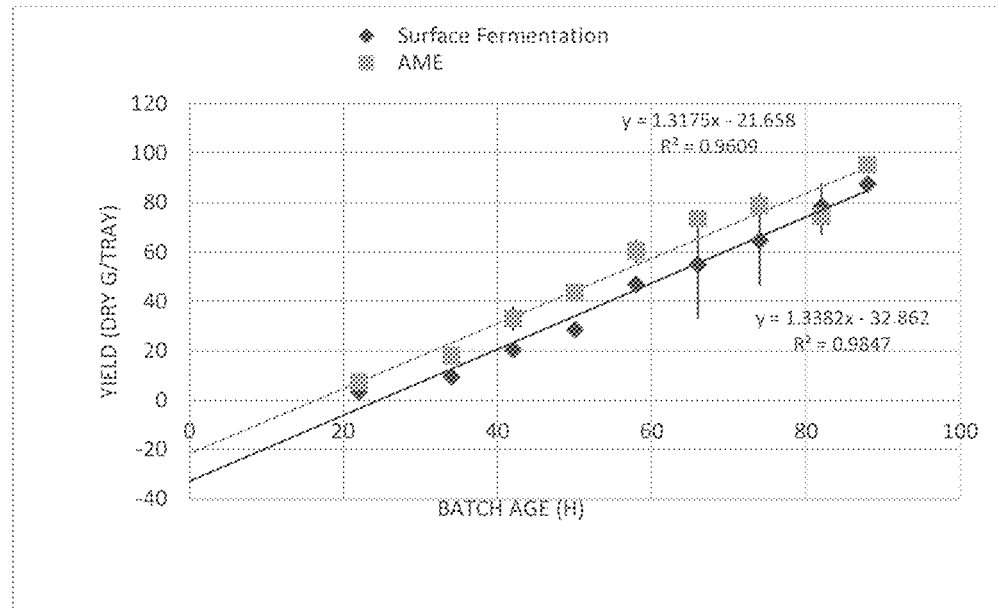
FIG. 3 is a graph of comparative growth for conventional surface fermentations and AMC fermentations.

An inoculum of MK7 ATCC Accession Deposit No. PTA-10698 was introduced onto the surface of each of six fermentation media in growth chambers: three conventional liquid media, and three AMCs according to the present invention. For each of the six media, the total volume of fermentation medium in the growth chamber was 1750 mL and the top surface area was 0.25 m$^2$. The fungi were then allowed to incubate on each medium for a period of 96 hours; starting at 36 hours after inoculation, total fungal growth was measured at intervals of six to eight hours. The results are presented in Table 3 and FIG. 3 (in FIG. 3, the mean growth from the three surface fermentations and the three AMC fermentations is given).

TABLE 3

| Time | Surface fermentation area yield (g/m$^2$, dry) | | | | AMC fermentation area yield (g/m$^2$, dry) | | | |
|---|---|---|---|---|---|---|---|---|
| (hours) | Tray 1 | Tray 2 | Tray | Mean | Tray 1 | Tray 2 | Tray 3 | Mean |
| 36 | 11.6 | 15.2 | 15.2 | 13.92 | 36.0 | 28.4 | 24.8 | 29.68 |
| 44 | 30.0 | 40.8 | 44.8 | 38.64 | 80.8 | 66.8 | 67.6 | 71.72 |
| 52 | 68.4 | 90.8 | 86.0 | 81.72 | 122.8 | 117.2 | 156.8 | 132.28 |
| 60 | 113.6 | 117.2 | 113.2 | 114.68 | 173.2 | 172.8 | 178.4 | 174.72 |
| 68 | 194.8 | 194.4 | 174.0 | 187.8 | 250.8 | 255.2 | 219.6 | 241.84 |
| 76 | 124.0 | 295.6 | 240.0 | 219.92 | 288.8 | 306.8 | 286.4 | 294.04 |
| 84 | 174.0 | 294.8 | 305.6 | 258.28 | 300.0 | 308.8 | 338.4 | 315.72 |
| 90 | 288.0 | 340.8 | — | 314.24 | 319.2 | 276.4 | — | 297.76 |
| 96 | — | — | 349.6 | 349.76 | — | — | 382.0 | 381.84 |

Example 3

This Example illustrates a comparison of fungal structure and composition between surface-fermented fungus and AMC-fermented fungus and demonstrates that AMC fungal fermentation processes can be utilized to provide markedly different fungal structure and composition than conventional surface fermentation processes.

Figure 4:
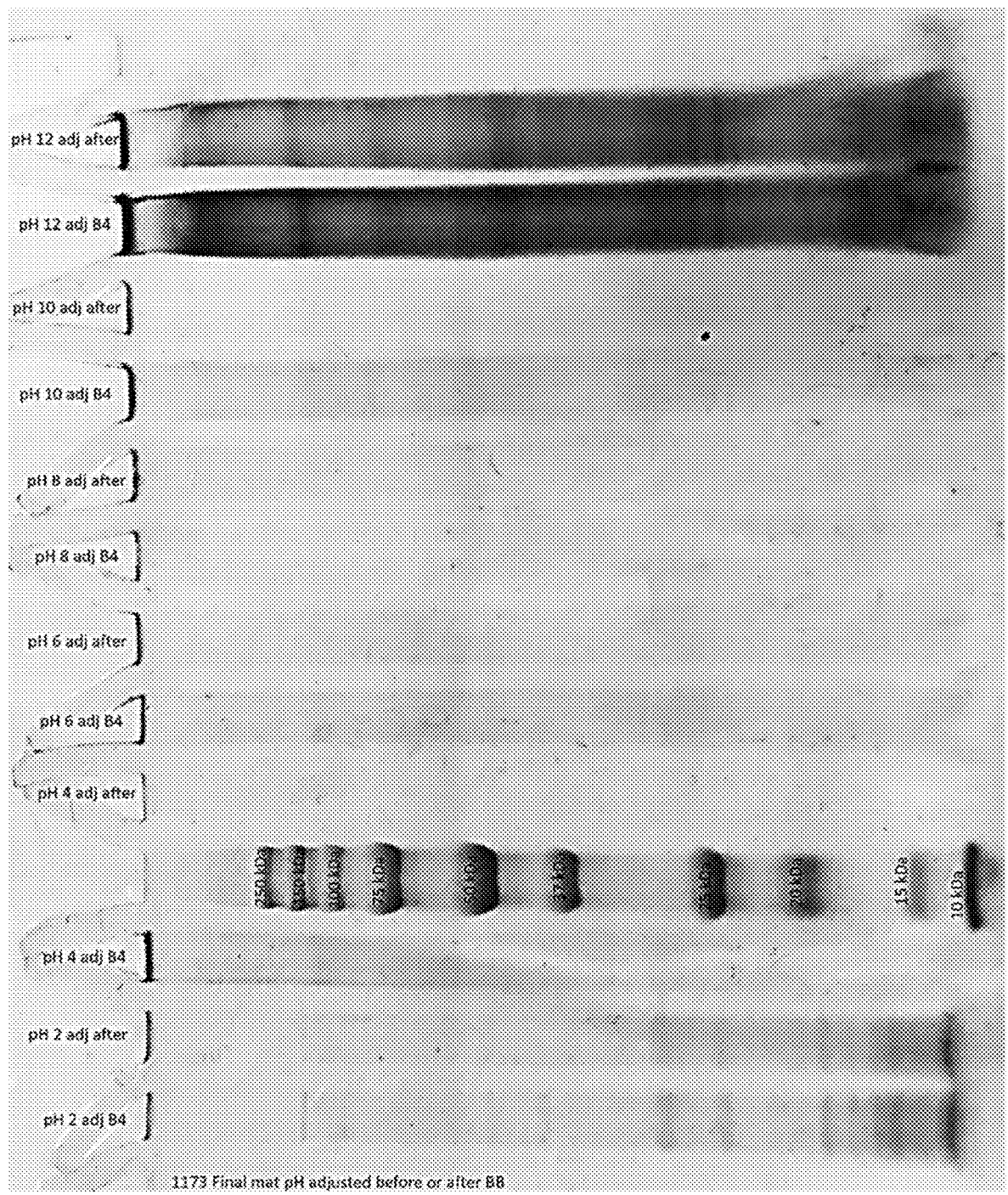
FIGS. 4 and 5 are protein assays of surface-fermented and AMC-fermented fungal specimens, respectively.

Extracts of the surface-fermented and AMC-fermented fungi grown in Example 2 were pH-buffered and subsequently assayed for protein content; the extracts were also lysed by bead beating, in some cases before and in some cases after pH adjustment. FIG. 4 shows results of these protein assays for the surface-fermented fungi, and FIG. 5 shows results of these protein assays for the AMC-fermented fungi (labeled "AME" in the figure).

Figure 5:
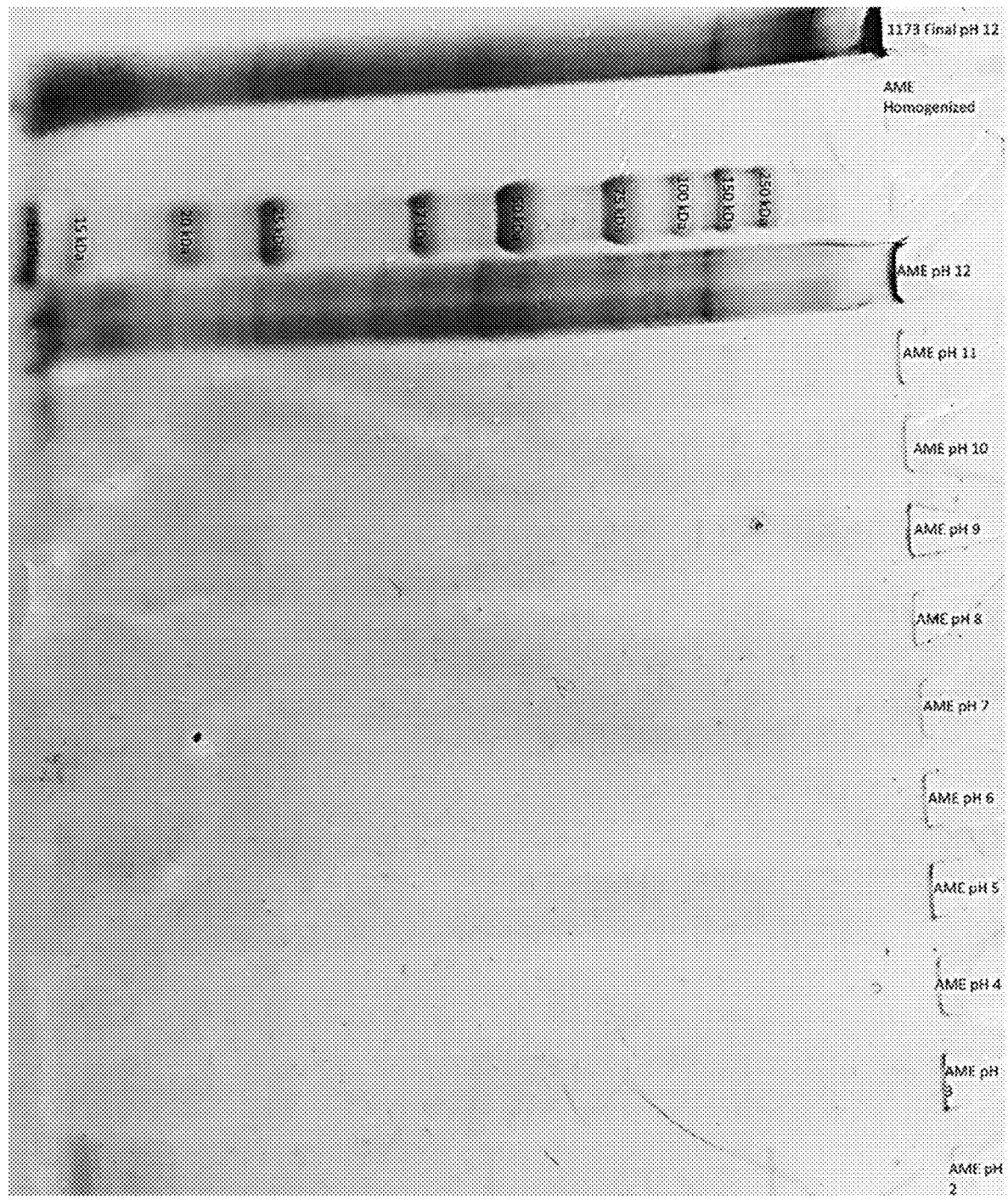

As FIGS. 4 and 5 illustrate, fungi produced by AMC fermentation have approximately double the extractable protein content of fungi produced by conventional surface fermentation. Without wishing to be bound by any particular theory, it is believed that this difference in protein content is due to a structural difference in the growth pattern of the two fermentation processes; specifically, it is believed that AMC fermentation results in a larger content of fungal hyphae, and a much lower content of microconidia, than conventional surface fermentation. The present inventors estimate that the fungus produced by AMC fermentation is approximately 1% microconidia, whereas the fungus produced by conventional surface fermentation is approximately 50% microconidia.

Another possible explanation for the difference in protein content between AMC-grown mats and mats grown by conventional surface fermentation, without wishing to be bound by any particular theory, is a difference in the fungal growth environment. In AMC fermentation, a large percentage of fungal growth occurs at the air/medium interface, e.g. on the surface of bubbles of air within the AMC; mycelia growing on such surfaces are exposed to differences in, for example, oxygen access and effective surface tension as compared to fungal tissues growing in a solution or underneath other mycelia. It may thus be possible that biomats grown on AMCs exhibit differences in, e.g., protein content due to an increased "surface effect," or in other words due to the fact that a greater share of the fungal biomass was grown on a surface rather than in solution or in an interior of a mycelial mass.

Example 4

Figure 6A:
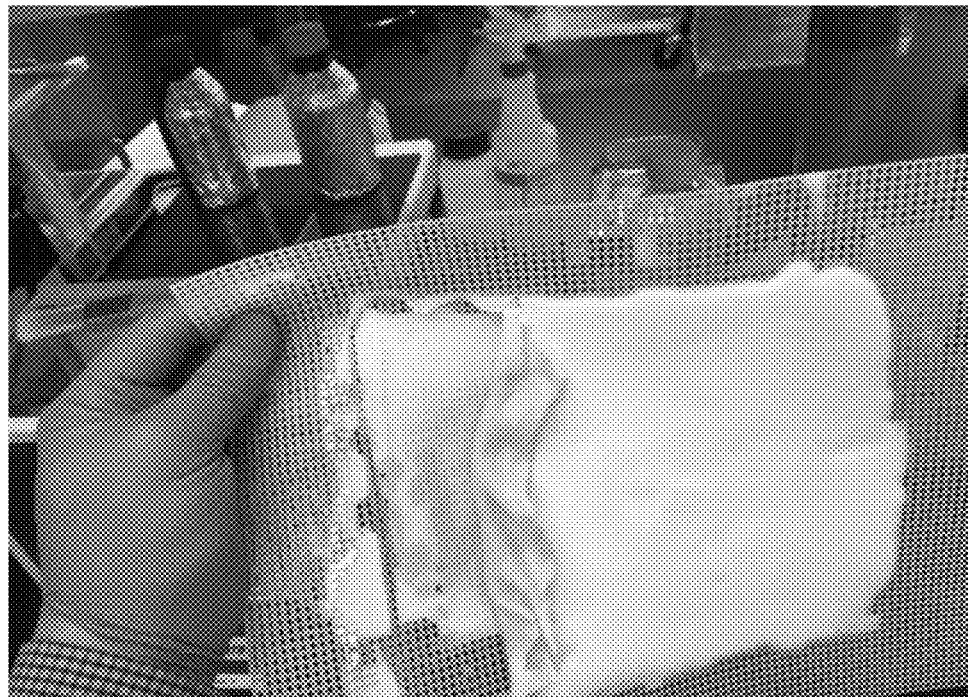
FIGS. 6A and 6B are top and bottom views, respectively, of a mesh substrate before harvesting of fungal biomats grown thereon.
Figure 6B:
Figure 7:
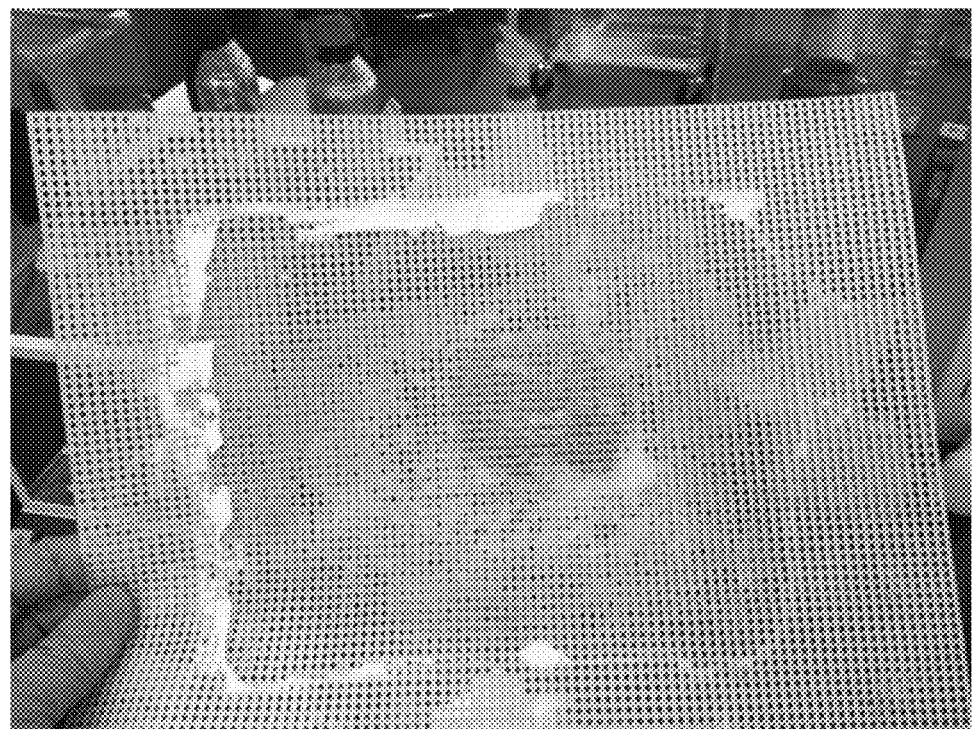
FIG. 7 is a view of the mesh substrate of FIGS. 6A and 6B after biomat harvesting.

This Example illustrates the use of AMCs of the present invention to promote fungal growth on the surface of a mesh substrate. 200 mL of a synergistically gelled AMC was prepared from inoculated MK102 growth medium by addition of gums (0.4 wt % locust gum, 0.2 wt % whey protein isolate) and a surfactant (0.4 wt % xanthan gum), followed by introduction of air via vortex using a KitchenAid immersion blender (10,000 rpm) for 60 seconds. The AMC was then applied to the surface of a 2 mm×2 mm hydrophobic polyolefin mesh that was supported by a scaffold; due to the high viscosity of the AMC, it was possible to spread the AMC on the surface of the mesh with no drainage or dripping. The mesh was then placed in an incubator at 27° C. for 72 hours, whereupon the fungal biomass was harvested from both top and bottom surfaces of the mesh. FIGS. 6A and 6B are top and bottom views, respectively, of the mesh substrate before harvesting, and FIG. 7 illustrates the mesh substrate after harvesting.

This test yielded a total fungal biomass of 26.556 g, with approximately equal masses of fungal biomass harvested from both the top and bottom surfaces of the mesh substrate. As FIGS. 6A and 6B illustrate, both mats were substantively identical, although the lower mat had a slightly greater moisture content (presumably due to gravity). After 45 minutes of steaming, the processed biomass had a visual appearance and an odor that were not apparently different from those of fungal biomass produced by conventional surface fermentation. This Example thus illustrates that, unlike conventional fermentation media that require a traditional container (dish, plate, tray, etc.), AMCs of the present invention can be used to culture filamentous fungi on surfaces, including porous surfaces, without flowing or drainage of the AMC.

Example 5

This Example illustrates the effects on fungal growth of various surfactants, thickeners or stabilizers, carbon sources, and growth medium salts.

MK102 growth medium was poured into each of several 5×7 glass trays and aerated to produce an AMC. Various additional gum products, emulsifiers, carbon sources, and so on were added to or modified in some samples, as shown in Table 4 below. The carbon source in each medium was present at 10 wt %. Each AMC was then inoculated with a fungal inoculum and allowed to incubate for 70 hours. Table 4 shows the yield and pH of the fungus produced from each AMC, as well as a subjective, binary indication of whether the color and smell of the biomass were or were not acceptable (i.e. sufficiently similar to surface fermentation). The volume of medium in each tray was 200 mL unless otherwise noted.

TABLE 4

| Sample | Yield (g) | pH | Color acceptable? | Smell acceptable? |
|---|---|---|---|---|
| MK103 NX200 | 56 | 2.76 | No | No |
| MK103 CX90 WPI | 18 | 5.30 | No | No |
| MK103 CX90 | 56 | 2.98 | No | No |
| MK103 NX200 GS | 42 | 2.98 | No | No |
| MK103 NX200 WPI | 68 | 3.27 | No | No |
| .5 G .5M NX200 | 25 | 6.71 | Yes | Yes |
| .5 G .5M NX200 LBG .5 V | 58 | 6.27 | Yes | Yes |
| .5 G .5M NX200 WPI | 40 | 5.97 | Yes | Yes |
| .5 G .5M NX200 LBG .25 V | 35 | n/a | Yes | Yes |
| Y-M+ WPI + 1 g fructose | 28 | 4.24 | Yes | Yes |
| Y-M+ CX90 WPI | 30 | 6.17 | Yes | Yes |
| Y-M+ NX200 WPI | 46 | 6.00 | Yes | Yes |
| Y-M+ WPI + 0.5 g fructose | 46 | 5.51 | Yes | Yes |
| MK102 + 1 g fructose | 48 | 5.74 | No | Yes |
| MK102 + 0.5 g fructose | 52 | 6.09 | No | Yes |

Legend: NX200, CX90 = xanthan gum (0.4 wt %)
LBG = locust bean gum (0.4 wt %)
WPI = whey protein isolate (0.2 wt %)
GS = glycerol stearate (AKA glycerol monostearate) (0.2 wt %)
.5 G .5M = 50% of glycerol in MK102 medium substituted with malt extract
Y-M+ = MK102 medium yeast extract replaced with malt extract
.25 V = ¼ volume (50 mL)
.5 V = ½ volume (100 mL)

Example 6

This Example illustrates the effects on fungal growth of various surfactants, thickeners or stabilizers, carbon sources, and growth medium salts.

The procedure of Example 5 was repeated, subject to the following modifications. None of the media used in Example 6 included nitrate salts; instead, the ammonium nitrate of typical MK102 growth medium was replaced with ammonium chloride at equal molarity. All media formulations contained 0.4 wt % NX200 xanthan gum, except for the formulations denoted "control." All results given in Table 5 are the average of two test runs, with the exception of the entries denoted by a superscript "1" (one test run) or "3" (three test runs, one resulting in no mat growth).

TABLE 5

| Carbon source | Additives | Yield (g) | pH | Color acceptable? | Smell acceptable? |
|---|---|---|---|---|---|
| 100% fructose | None | 24.553 | 2.09 | Yes | Yes |
| | GS | 17.947 | 2.00 | Yes | Yes |
| | WPI | 17.156 | 2.04 | Yes | Yes |
| | LBG | 16.343 | 1.96 | Yes | Yes |
| | LBG + GS | 18.254 | 2.00 | Yes | Yes |
| | Control[1] | 9.080 | 2.16 | Yes | Yes |
| 50% malt extract 50% glycerol | None | 9.745 | 2.12 | Yes | Yes |
| | GS[1] | 13.266 | 2.20 | Yes | Yes |
| | WPI | 13.390 | 2.16 | Yes | Yes |
| | LBG | 9.595 | 2.15 | Yes | Yes |
| | LBG + GS | 17.295 | 2.16 | Yes | Yes |
| | Control[1] | 0.000 | n/a | n/a | n/a |
| 100% malt extract | None | 15.511 | 2.46 | Yes | Yes |
| | GS | 12.002 | 2.28 | Yes | Yes |
| | LBG[1] | 10.922 | 2.27 | Yes | Yes |
| | LBG + GS[1] | 23.862 | 2.60 | Yes | Yes |
| | WPI | 13.158 | 2.27 | Yes | Yes |
| | Control[1] | 8.757 | 2.50 | Yes | Yes |

TABLE 5-continued

| Carbon source | Additives | Yield (g) | pH | Color acceptable? | Smell acceptable? |
|---|---|---|---|---|---|
| 100% glycerol | None | 9.496 | 2.27 | Yes | Yes |
| | GS | 9.912 | 2.21 | Yes | Yes |
| | WPI | 12.092 | 2.20 | Yes | Yes |
| | LBG | 11.020 | 1.99 | Yes | Yes |
| | LBG + GS[1] | 10.391 | 2.12 | Yes | Yes |
| | Control[1] | 0.000 | n/a | n/a | n/a |
| MK102 control[3] | | 32.999 | 3.30 | Yes | Yes |

Example 7

This Example illustrates the effects on fungal growth of various surfactants, thickeners or stabilizers, carbon sources, and growth medium salts.

The procedure of Example 5 was repeated, subject to the following modifications. The total incubation time was modified to 48, 68, or 72 hours, as shown in Table 6. The carbon source for the test runs was 100% fructose (M1 and M2), 50% fructose/50% glycerol (M3 and M4), or 100% glycerol (M5 and M6). In the media used in Example 7, the ammonium nitrate of typical MK102 growth medium was replaced with potassium nitrate at either one-half (M1, M3, M5) or equal (M2, M4, M6) molarity. 100 mL of growth medium was used in each test tray. Various parameters of the fungal biomass obtained from these tests are given in Table 6; results given for media without glycerol monostearate additive are the average of two test runs (except for medium M2), while results given for medium M2 and media with glycerol monostearate additive are for a single test run.

TABLE 6

| Medium | Additive | Time (hours) | Initial pH | Final pH | Yield (g) | Waste (mL) |
|---|---|---|---|---|---|---|
| M1 | None | 72 | 3.25 | 1.41 | 20.751 | 17 |
| | GS | 72 | 3.25 | 1.40 | 20.550 | 32 |
| M2 | None | 72 | 3.25 | 3.15 | 50.304 | 1 |
| | None | 48 | 3.25 | 2.88 | 32.67 | 0 |
| | GS | 72 | 3.25 | 2.67 | 44.77 | 3 |
| M3 | None | 72 | 3.25 | 1.72 | 20.19 | 43 |
| | GS | 72 | 3.25 | 1.74 | 21.055 | 15 |
| M4 | None | 68 | 3.25 | 2.25 | 38.427 | 8 |
| | GS | 72 | 3.25 | 1.89 | 35.03 | 12 |
| M5 | None | 72 | 3.25 | 2.76 | 24.602 | 31 |
| | GS | 72 | 3.25 | 1.91 | 25.416 | 12 |
| M6 | None | 72 | 3.25 | 5.21 | 20.293 | 38 |
| | GS | 72 | 3.25 | 3.65 | 21.576 | 30 |
| Control | None | 72 | 3.25 | 4.61 | 24.924 | 32 |
| | GS | 72 | 3.25 | 3.24 | 25.724 | 22 |

As Table 5 shows, culture M2 without glycerol monostearate additive over 72 hours produced the highest yield, while culture M2 without glycerol monostearate additive over 48 hours outperformed control cultures over 72 hours.

Example 8

This Example illustrates a process for making fungal biomats using both an AMC process and a conventional liquid surface fermentation (LSF) process.

All components of M2 medium as defined in Table 7 below (on a basis of 120 liters of total medium), except for fructose, were added to a boilermaker in amounts sufficient to provide 80 liters of medium, and the medium was brought to a boil. 10 liters of the boiling medium was pumped into each of eight separate pots. Fructose was added to each of these separate pots in varying amounts to provide two pots containing each of four fructose concentrations (7.5%, 10%, 15%, and 20% w/v, respectively corresponding to molar carbon-to-nitrogen ratios in the medium of 8.24, 10.99, 16.48, and 21.98). Each pot of medium was intermittently stirred until the fructose was fully dissolved, whereupon the pot was covered with a lid and sealed with plastic wrap. Each pot was allowed to cool overnight to room temperature. The following day, the pH of the medium in each pot was adjusted to pH 3.5 with phosphoric acid. Fungal inoculum was then added to each pot in an amount of 5% v/v. One pot at each fructose concentration was mixed using a high-speed disperser (HSD) at 5,000 rpm, with 0.4% w/v of xanthan gum added during mixing. From each of the eight pots of medium, 2 liters of medium were poured into each of five separate flat trays having a surface area of 0.25 m². These 40 total trays were then placed on racks in a chamber maintained at a temperature of 31° C. and 88% relative humidity, and the fungal organism was allowed to grow for 96 hours under these conditions.

TABLE 7

| Ingredient | Amount |
|---|---|
| Potassium nitrate | 756 g |
| Ammonium chloride | 813.6 g |
| Urea | 410.7 g |
| Calcium chloride | 159 g |
| Magnesium sulfate heptahydrate | 120 g |
| Monopotassium phosphate | 480 g |
| Trace EDTA | 48 mL |
| Fructose | 9.000 kg (for 7.5 wt %) |
| | 12.000 kg (for 10 wt %) |
| | 18.000 kg (for 15 wt %) |
| | 24.000 kg (for 20 wt %) |
| Yeast extract | 180 g |
| Water | 120 L |

Example 9

This Example illustrates the effects on raw biomat thickness of carbon concentration and/or carbon-to-nitrogen ratio in both AMCs and conventional LSF media.

The biomats produced in Example 8 were removed from the trays. The thickness of each mat was measured at three separate points: on an edge of the mat, in the center of the mat, and at a non-central interior portion of the mat. This yielded a total of fifteen raw mat thickness measurements for each of the eight medium types, i.e. 120 thickness measurements in total. The results of these raw mat thickness measurements are illustrated in FIG. 8.

Figure 8:
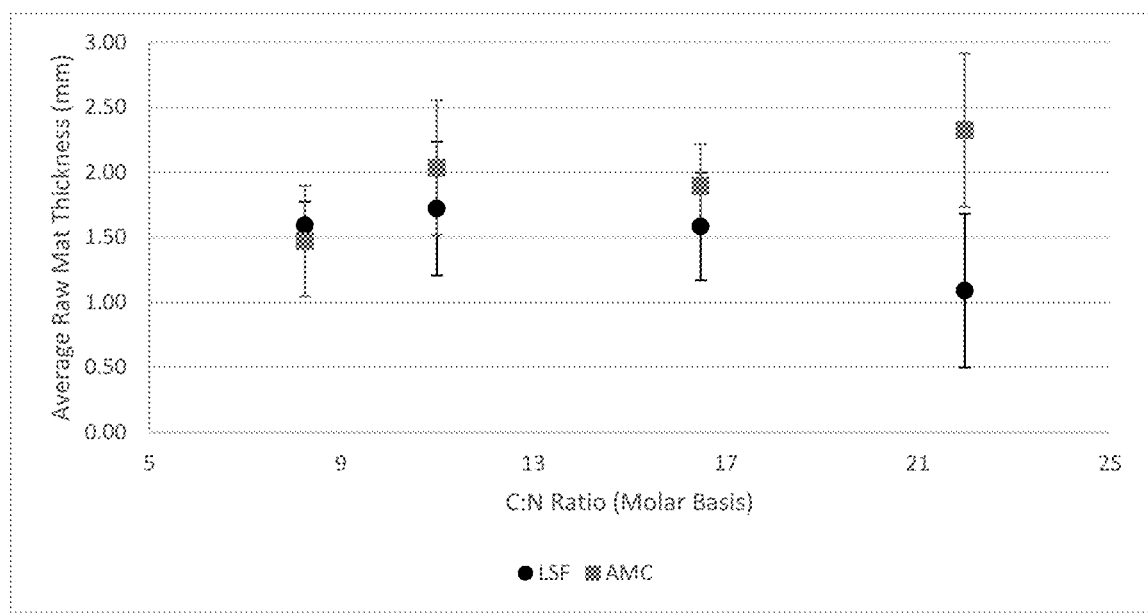
FIG. 8 is a graph showing the effect of carbon concentration and/or carbon-to-nitrogen ratio, in both AMCs and conventional liquid surface fermentation (LSF) media, on biomat thickness.

As FIG. 8 illustrates, samples grown on AMCs displayed a trend of increasing thickness with increasing fructose (i.e. carbon) concentration. Samples grown on LSF media displayed an increase in thickness as fructose concentration increased from 7.5% to 10%, but then a decrease in thickness with increasing fructose concentration such that the lowest thickness was observed at the highest (20%) fructose concentration.

Example 10

This Example illustrates the effects on area yield and biomat density of carbon concentration and/or carbon-to-nitrogen ratio in both AMCs and conventional LSF media.

Using a knife, each of the 40 biomats produced in Example 8 was cut into quarters, yielding a total of 20 mat specimens for each of the eight different medium types; of these 20 specimens for each medium type, two randomly selected specimens were placed in freezer bags and frozen for later microscopy testing, while the remaining 18 specimens were boiled in water for 30 minutes and then soaked in deionized water at 70° C., with intermittent stirring, for an additional 30 minutes. Of the 18 boiled specimens for each medium type, four were dehydrated at 160° F. for 23 hours and then weighed. The average area yield (i.e. dry mass of biomat per area of fermentation tray) of these four specimens for each of the medium types is illustrated in FIG. 9, and the average dry density for these specimens is illustrated in FIG. 10.

Figure 9:
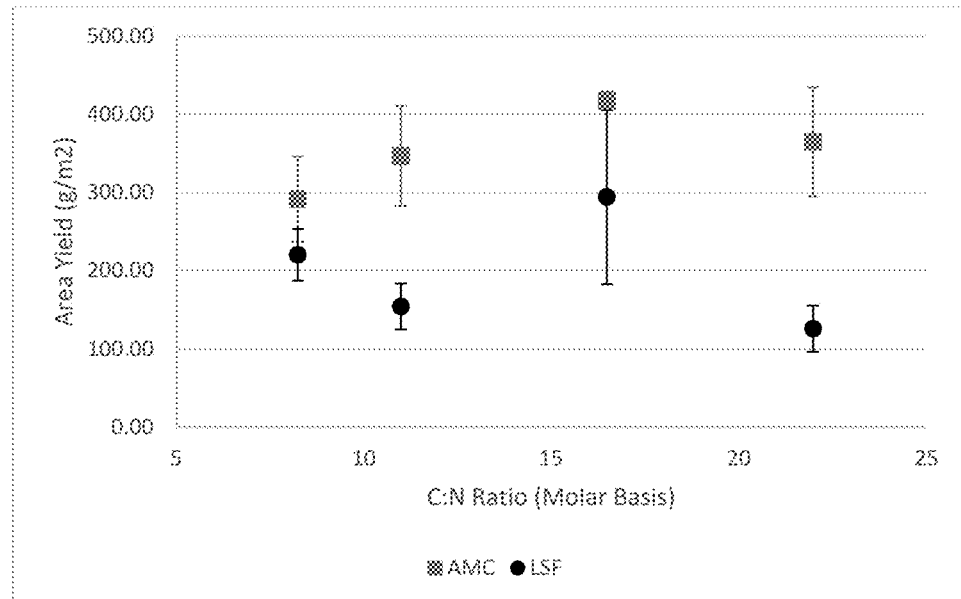
FIG. 9 is a graph showing the effect of carbon concentration and/or carbon-to-nitrogen ratio, in both AMCs and conventional LSF media, on biomat area yield.
Figure 10:
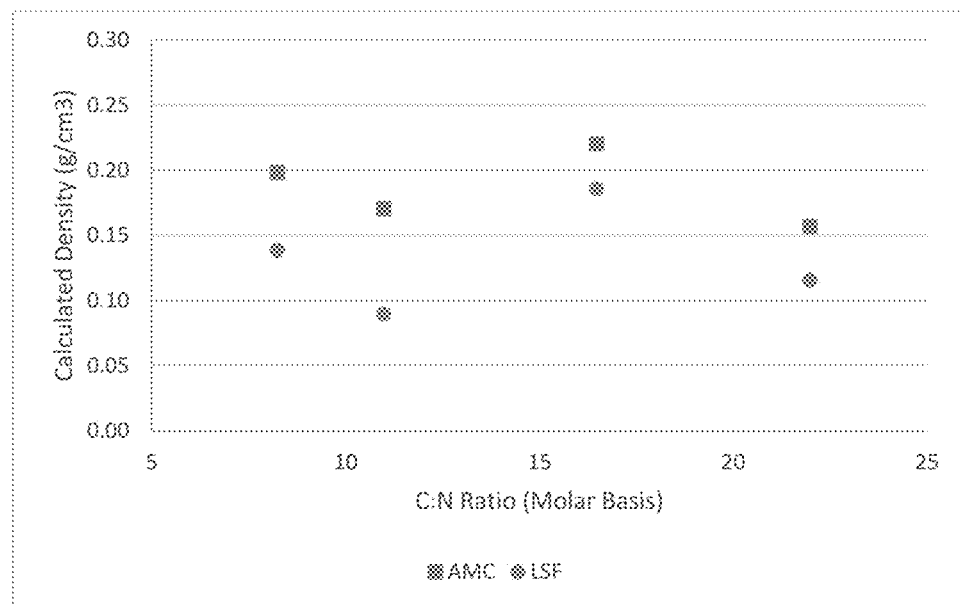
FIG. 10 is a graph showing the effect of carbon concentration and/or carbon-to-nitrogen ratio, in both AMCs and conventional LSF media, on biomat density.

As FIG. 9 illustrates, there are notable differences in area yield between biomats grown on AMCs and those grown on conventional LSF media. Most strikingly, at all fructose concentrations, and especially those higher than 7.5%, area yield is significantly greater for biomats grown on AMCs than for those grown on LSF media. Additionally, while LSF mats have no discernible trend of yield with fructose concentration (suggesting that conditions other than carbon concentration and/or carbon-to-nitrogen ratio play a greater role in area yield for LSF processes), for AMC mats there is an obvious trend in which yield increases with increasing fructose concentration up to about 15%, then decreases slightly as fructose concentration is further increased to 20%. This finding suggests that area yield, like raw mat thickness, can be effectively controlled by controlling the carbon concentration and/or carbon-to-nitrogen ratio of the growth medium. These trends are further illustrated in FIG. 10, in which the density of both AMC and LSF mats does not appear to increase or decrease predictably with fructose concentration, although, interestingly, whatever trends exist appear to be the same for both AMC and LSF mats.

Example 11

This Example illustrates the effects of carbon concentration and/or carbon-to-nitrogen ratio on the tensile strength and strain at break of boiled AMC- and LSF-grown biomats.

Of the 18 boiled specimens for each medium type produced in Example 10, four were cut into pieces for testing of their mechanical properties, particularly their tensile strength and strain at break. The average tensile strength of these four specimens for each of the medium types is illustrated in FIG. 11, and the average strain at break for these specimens is illustrated in FIG. 12.

Figure 11:
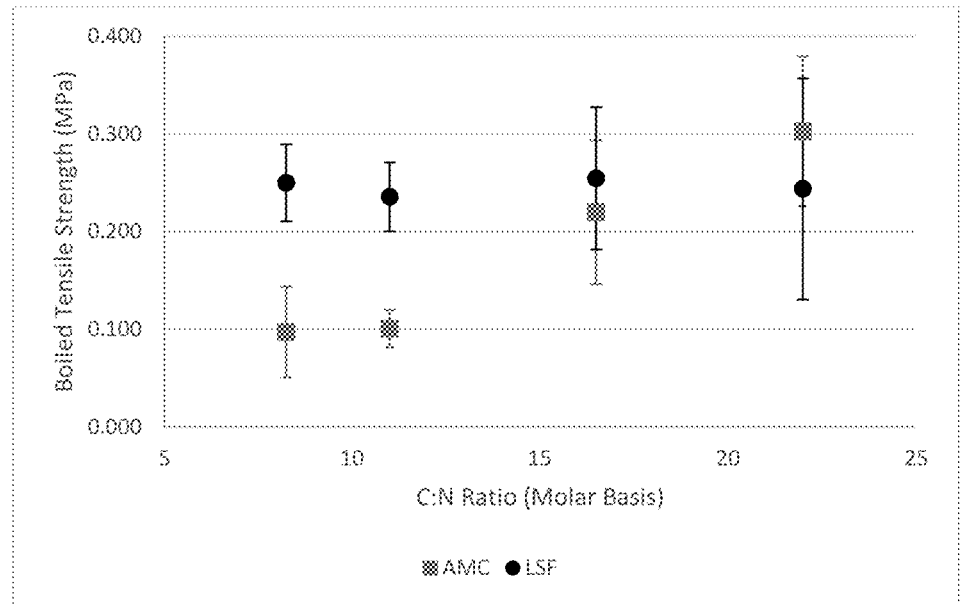
FIG. 11 is a graph showing the effect of carbon concentration and/or carbon-to-nitrogen ratio, in both AMCs and conventional LSF media, on biomat tensile strength.

As FIG. 11 illustrates, biomats grown on AMCs display a trend of increasing tensile strength with increasing fructose (i.e. carbon) concentration, while biomats grown using LSF media had consistent tensile strengths substantially independent of fructose concentration. As a result of these trends, at low fructose concentrations, mats grown on AMCs generally have tensile strengths below those grown on LSF media, but as fructose concentration increases, this difference narrows, and at the highest fructose concentrations the tensile strength of mats grown on AMCs overtakes that of mats grown on LSF media. This once again demonstrates that mechanical and material properties of fungal biomats can be effectively controlled by controlling the carbon concentration and/or carbon-to-nitrogen ratio in AMCs on which the biomats are grown.

Figure 12:
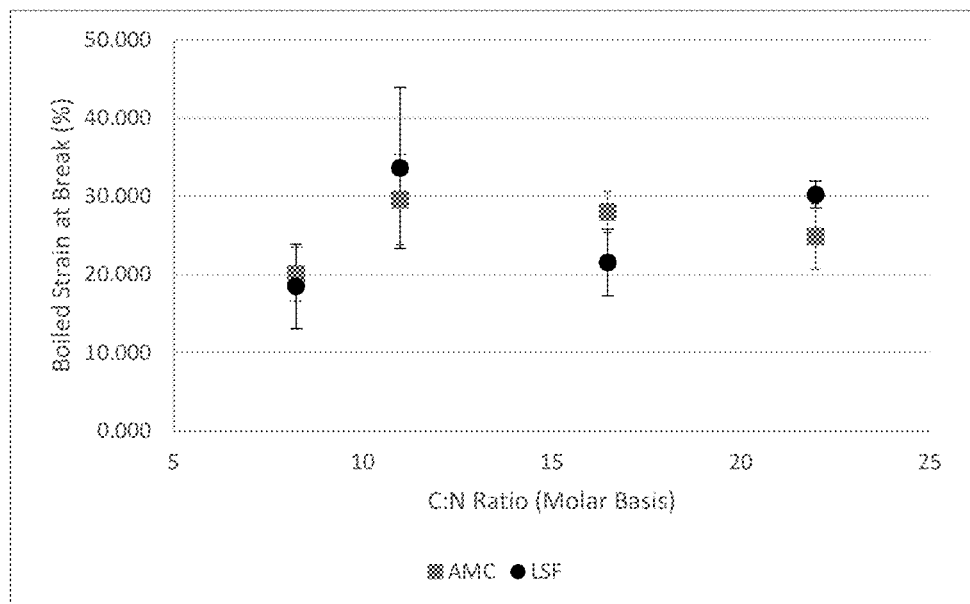
FIG. 12 is a graph showing the effect of carbon concentration and/or carbon-to-nitrogen ratio, in both AMCs and conventional LSF media, on biomat strain at break.
Figure 13A:
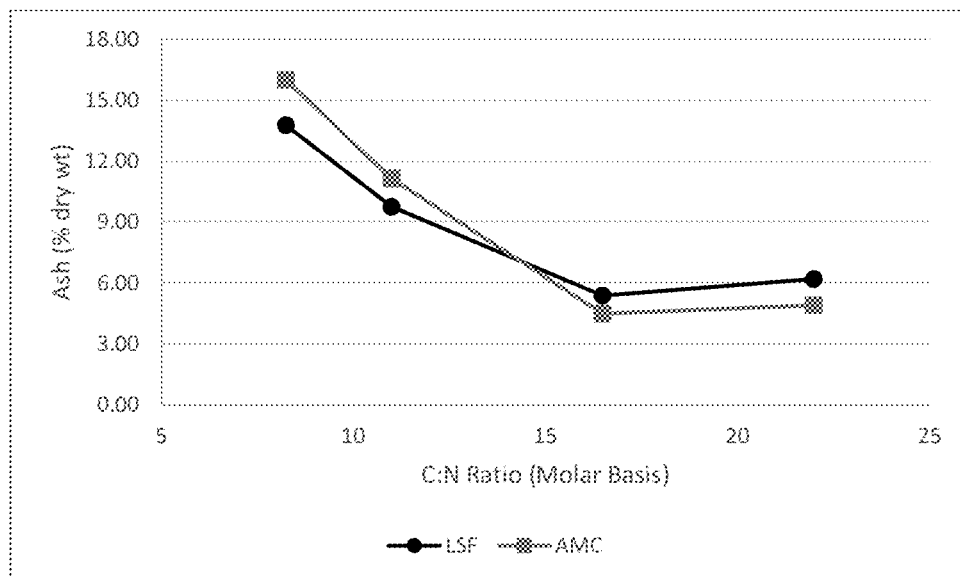
FIGS. 13A through 13D are graphs showing the effect of carbon concentration and/or carbon-to-nitrogen ratio, in both AMCs and conventional LSF media, on biomat ash, carbohydrate, fat, and protein content, respectively.
Figure 13B:
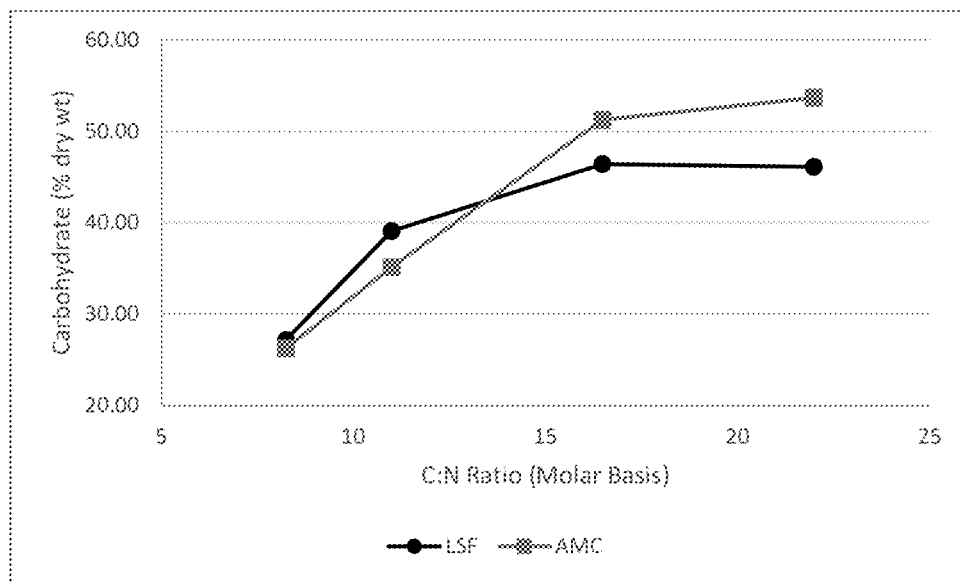
Figure 13C:
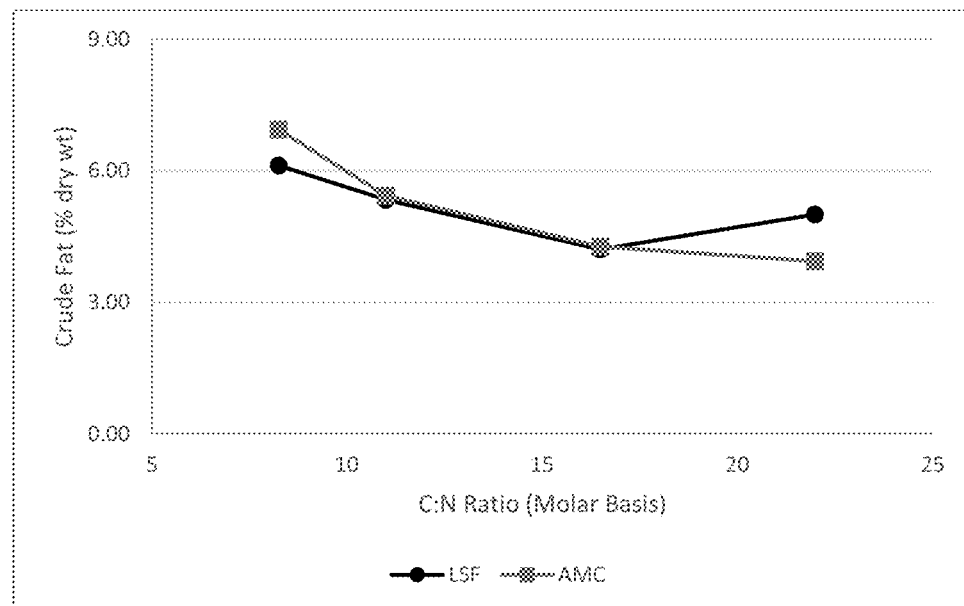
Figure 13D:
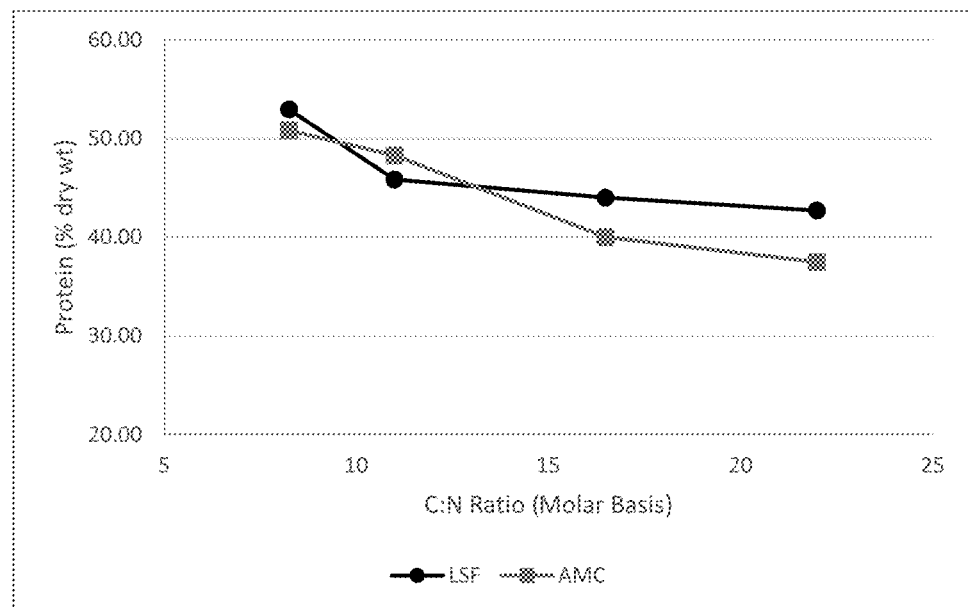

As FIG. 12 illustrates, there is no clear trend in strain at break as a function of fructose concentration for either AMC-grown or LSF-grown biomats. Interestingly, however, the strains at break of AMC-grown and LSF-grown biomats appear to be largely comparable at all fructose concentrations. Additionally, without wishing to be bound by any particular theory, the fact that both types of biomat have their lowest strain at break at the lowest fructose concentration (7.5%) but their highest strain at break at the next lowest concentration (10%) may be explained by the phenomenon of autolysis of cellular structures as a result of exhaustion of the primary carbon source; at very low carbon concentrations and/or carbon-to-nitrogen ratios, this autolysis may be significant enough to result in wholesale degradation and thus weakening at the entire mat, whereas a slightly lesser degree of autolysis at a slightly higher fructose concentration may provide just enough autolysis to allow for greater freedom of movement of fungal filaments under strain without compromising the structures to such an extent as to result in total material failure.

Example 12

This Example illustrates the effects of carbon concentration and/or carbon-to-nitrogen ratio on nutritional content in both AMC-grown and LSF-grown fungal biomats.

Of the 18 boiled specimens for each medium type produced in Example 10, two were chopped into small pieces and frozen in 50 mL conical tubes for compositional analysis (protein, moisture, fat, ash, and carbohydrates). The average contents in these samples of ash (after combustion), carbohydrates, crude fat, and protein is illustrated in FIGS. 13A through 13D, respectively.

As FIGS. 13A through 13D illustrate, the nutritional compositions of AMC-grown and LSF-grown biomats generally follow similar trends. For both types of mat, a general decrease in ash, fat, and protein contents as fructose (i.e. carbon) concentration increases is observed, except for possible slight increases in ash, and for AMC-grown mats in fat, at the highest fructose concentrations (15% to 20%). The opposite trend is observed with respect to carbohydrate content, which increases markedly in both AMC- and LSF-grown mats as fructose concentration increases. Without wishing to be bound by any particular theory, the present inventors believe this increase in carbohydrate content is the cause for the positive trend in tensile strength with increasing fructose concentration that was observed in AMC-grown mats in Example 11, though why this same trend was not also observed with respect to LSF-grown mats is unclear.

Additionally, without wishing to be bound by any particular theory, it is believed that the boiling of the mats used in this Example accounts for the largely similar protein contents of the AMC- and LSF-grown mats, as opposed to the marked differences observed in Example 3. Specifically, the boiling of the mats prior to assaying likely results in a significant fraction of the additional protein in the AMC-grown mats being washed away or otherwise lost to the water used for the boil.

Example 13

This Example illustrates a process for making AMCs for fungal biomat growth using various aeration and mixing techniques and devices.

Biomats were produced according to the procedure described in Example 8, except that the amount of fructose in each batch of growth medium was 15% w/v and all batches were aerated and mixed with 0.4% w/v xanthan gum to create AMCs; in this Example, the variable that differentiated the various AMCs was the mixing device used to aerate the fermentation medium to create the AMC. Specifically, three different mixing devices were used: a high-speed disperser (HSD) at 5,000 rpm, a high-shear mixer (HSM) at 10,000 rpm, and a KitchenAid kitchen mixer with a whisk attachment at a speed setting of 9 out of 10. AMCs made with the kitchen mixer were prepared in smaller batches (2 liters or less) due to the limited volume of the mixing vessel.

Example 14

This Example illustrates the effects on raw biomat thickness and biomat area yield and density of the mixing technique and device used to prepare the AMCs on which the biomats were grown.

The thickness of the biomats produced in Example 13 was measured according to the procedure described in Example 9, and the area yield and density of the mats was measured according to the procedure described in Example 10. The results of the raw mat thickness measurements are illustrated in FIG. 14, and the results of the area yield and density measurements are illustrated in FIGS. 15A and 15B, respectively.

Figure 14:
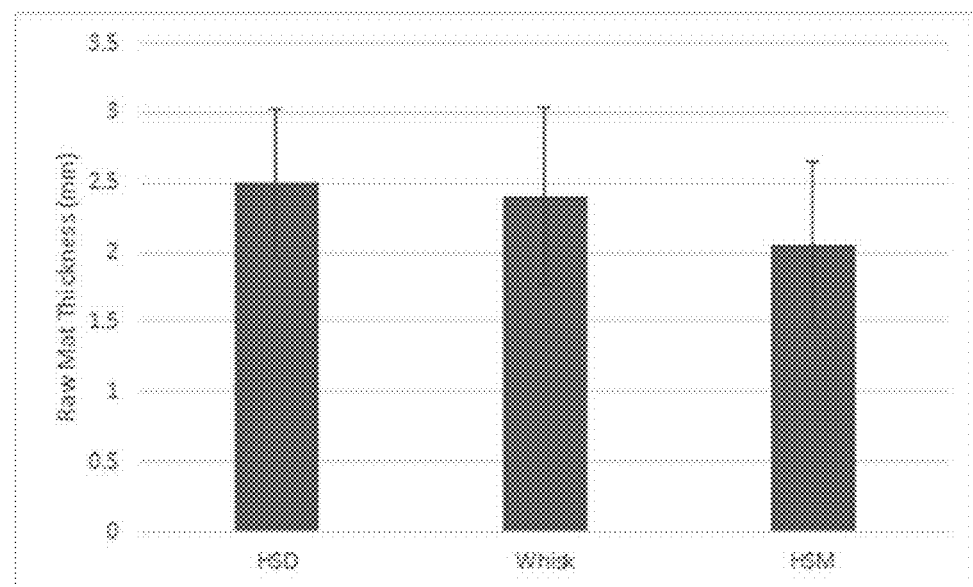
FIG. 14 is a graph showing the effect of mixing technique/device used to prepare AMCs on biomat thickness.
Figure 15A:
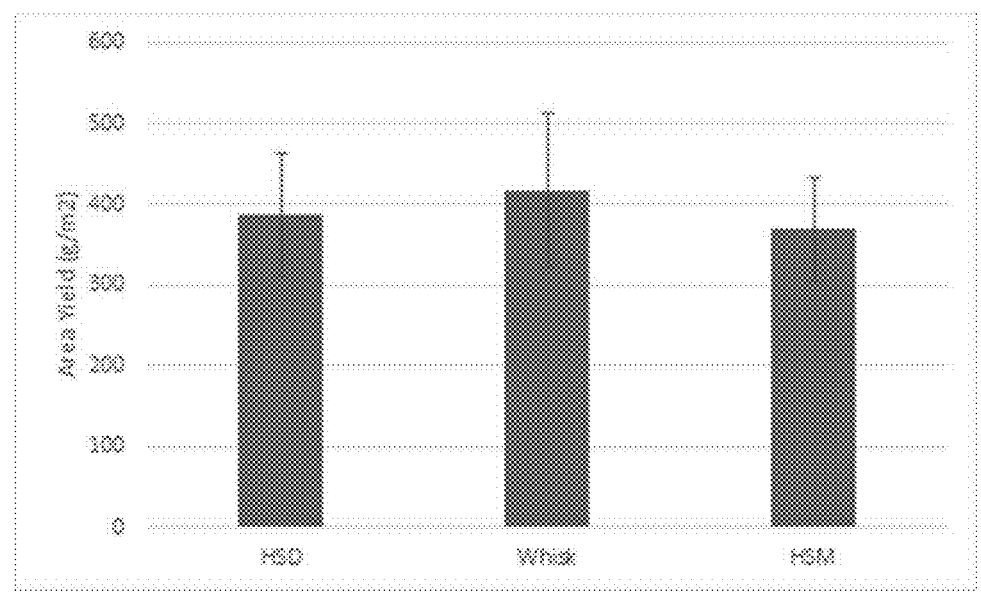
FIGS. 15A and 15B are graphs showing the effect of mixing technique/device used to prepare AMCs on biomat area yield and density, respectively.
Figure 15B:
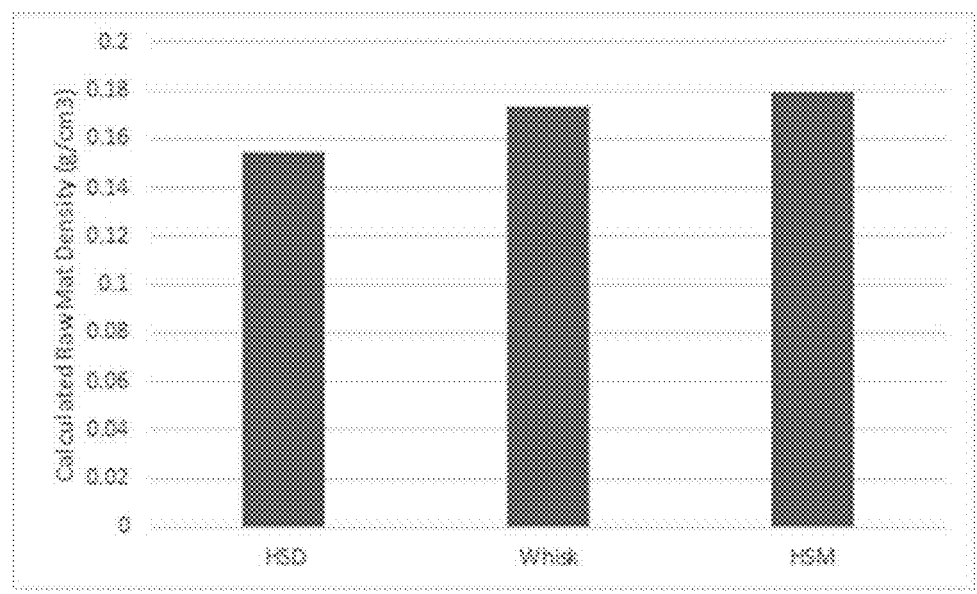

As FIG. 14 illustrates, the thicknesses of all mat samples prepared in this Example were largely similar. The only statistically significant difference in thickness can be observed between mats grown on HSD AMCs and those grown on HSM AMCs; the HSD AMCs produced the thickest mats, while the HSM AMCs produced the thinnest mats. All samples had statistically similar area yields and mass densities. Without wishing to be bound by any particular theory, it is believed that the device or techniques used to aerate the fermentation medium to produce the AMC is not as crucial to the thickness, yield, or density of the resulting biomat as the ability of the medium itself to support a biomat on the liquid-air interface.

Example 15

This Example illustrates the effects of the mixing technique/device used to prepare the AMCs on which fungal biomats are grown on the tensile strength and strain at break of the resulting boiled biomats.

The tensile strength and strain at break of the biomats produced in Example 13 was measured according to the procedure described in Example 11. The average tensile strength of the tested mats is illustrated in FIG. 16, and the average strain at break for these specimens is illustrated in FIG. 17.

Figure 16:
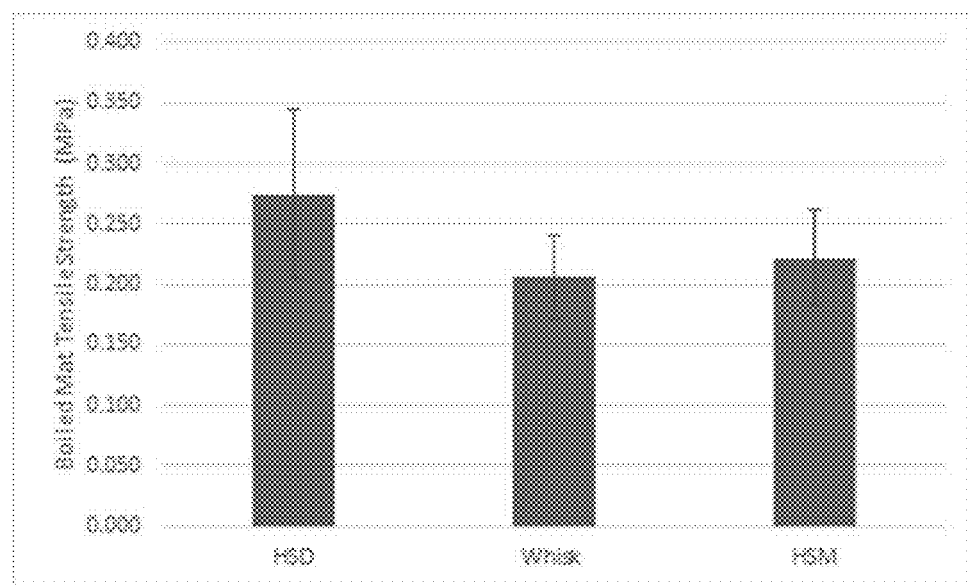
FIG. 16 is a graph showing the effect of mixing technique/device used to prepare AMCs on biomat tensile strength.
Figure 17:
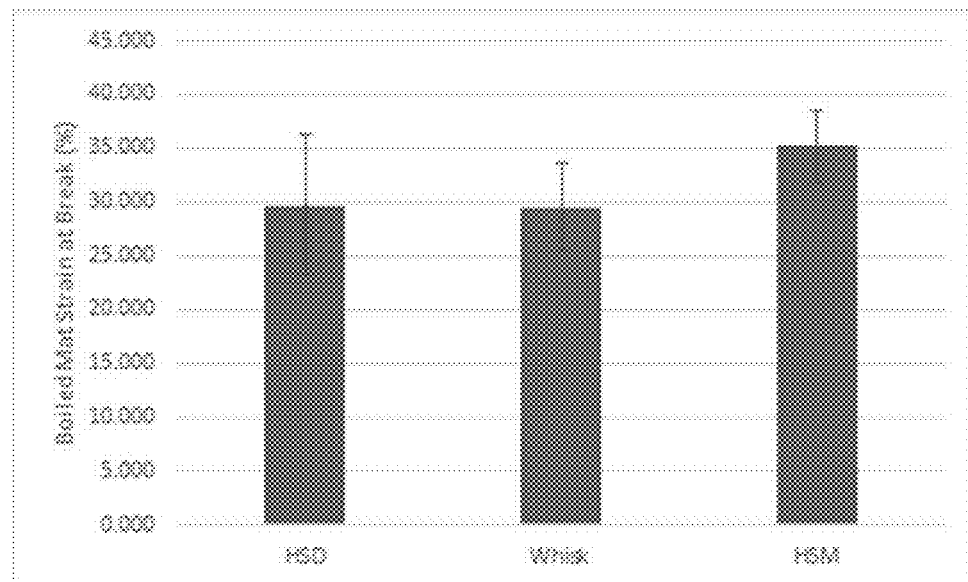
FIG. 17 is a graph showing the effect of mixing technique/device used to prepare AMCs on biomat strain at break.

As FIGS. 16 and 17 illustrate, mats produced from each of the three types of AMC (HSD, kitchen mixer with whisk attachment, and HSM) were largely similar in their material and mechanical properties. However, one notable relationship can be observed in comparing the two figures: there is generally an inverse relationship between the tensile strength and the strain at break for any particular mixing technique/device; mats produced from HSM AMCs had the highest strain at break but the lowest tensile strength, while mats produced from HSD AMCs had the highest tensile strength but the lowest strain at break.

Example 16

This Example illustrates a process for making AMCs for fungal biomat growth using various stabilizers, surfactants, and thickeners.

Biomats were produced according to the procedure described in Example 8, except that the amount of fructose in each batch of growth medium was 15% w/v and all batches were aerated using a high-shear mixer at 10,000 rpm; in this Example, the variable that differentiated the various AMCs was the gum or other thickener or stabilizer mixed during aeration to form the AMC. Specifically, six AMCs were prepared, respectively containing as stabilizer/thickener 0.4% w/v xanthan gum, 1.5% w/v carboxymethyl cellulose (CMC), 1% w/v konjac root, 1.5% w/v guar gum, 1.5% w/v arabic gum, and 1% w/v tara gum.

Qualitative assessment of the six types of AMCs and the biomats produced thereon revealed notable differences. A thickener of 0.4% w/v xanthan gum formed a medium-viscosity liquid that upon aeration formed a highly stable AMC with a large volume fraction of trapped air. A thickener of 1.5% w/v CMC formed only a semi-stable foam on the surface of the fermentation medium (i.e. without trapped air in the bulk of the liquid medium); biomats grew unevenly and thinly on this substrate. A thickener of 1% w/v konjac root formed a more stable foam to a greater depth in the liquid medium relative to CMC, but foam formation was still incomplete, and slow dissolution of the konjac led to a low-viscosity substrate that produced inconsistent biomats (and, in the case of two trays, failure to grow any biomat at all). A thickener of 1.5% w/v guar gum dissolved slowly at first, resulting in an initially low-viscosity substrate that thickened so substantially as to become nearly gel-like; biomats grown on this substrate were consistently thick and relatively dry, and had high bending rigidity. A thickener of 1.5% w/v arabic gum failed to result in a stable foam; of the four trays using this AMC, two yielded no biomat and the other two yielded only very thin mats. A thickener of 1% w/v tara gum formed a highly viscous and stable AMC that consistently yielded very thick mats with notably light and "fluffy" fungal hyphae.

Example 17

This Example illustrates the effects on raw biomat thickness and biomat area yield and density of the thickener used to prepare the AMCs on which the biomats were grown.

The thickness of the biomats produced in Example 16 was measured according to the procedure described in Example 9, and the area yield and density of the mats was measured according to the procedure described in Example 10. The results of the raw mat thickness measurements are illustrated in FIG. 18, and the results of the area yield and density measurements are illustrated in FIGS. 19A and 19B, respectively.

Figure 18:
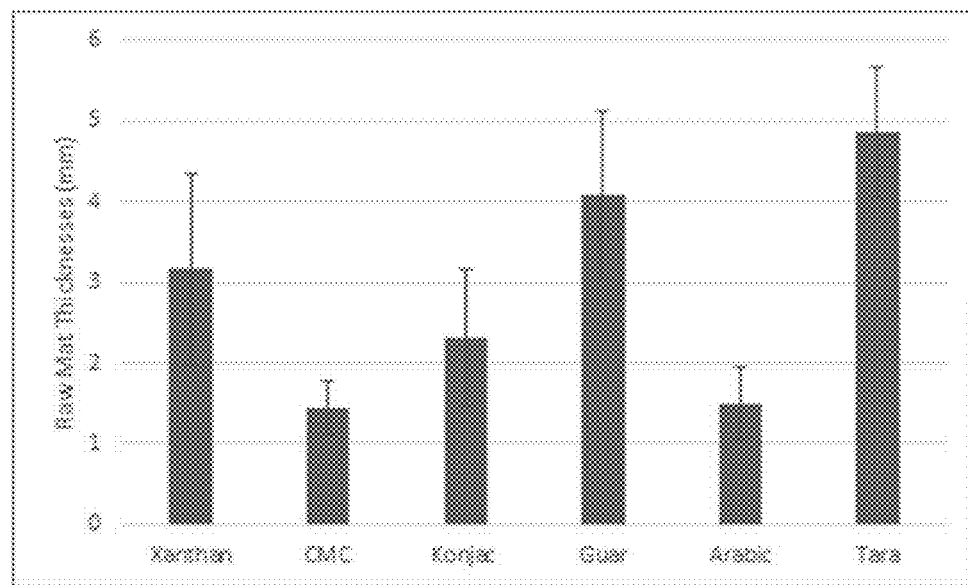
FIG. 18 is a graph showing the effect of AMC thickener on biomat thickness.
Figure 19A:
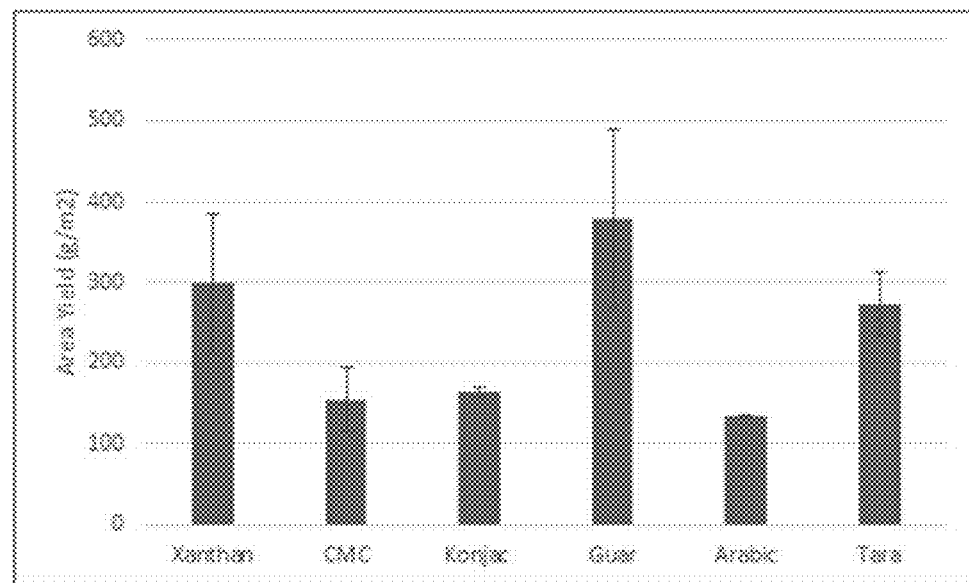
FIGS. 19A and 19B are graphs showing the effect of AMC thickener on biomat area yield and density, respectively.
Figure 19B:
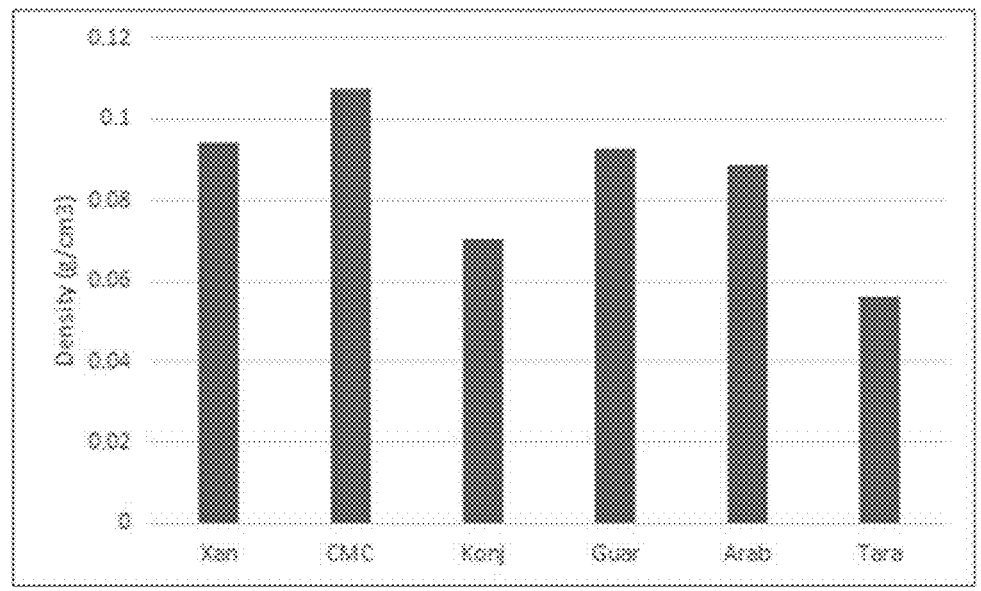

As FIG. 18 illustrates, the thickness of biomats was greatly affected by the thickener used to produce the AMC on which the mats were grown. High-thickness mats were obtained from AMCs containing xanthan gum, guar gum, or tara gum, all of which were medium- or high-viscosity AMCs; without wishing to be bound by any particular theory, it is hypothesized that fungal biomat growth is most effectively promoted when the fungus is physically supported on the air-medium interface. As FIG. 19A illustrates, area yields followed a similar trend as mat thickness. As FIG. 19B illustrates, mat density was generally fairly stable and independent of the thickener used, except for mats grown on the tara gum AMC, which were notably less dense than mats grown on other AMCs.

Example 18

This Example illustrates the effects of the thickener used to prepare the AMCs on which fungal biomats are grown on the tensile strength and strain at break of the resulting boiled biomats.

The tensile strength and strain at break of the biomats produced in Example 16 was measured according to the procedure described in Example 11. The average tensile strength of the tested mats is illustrated in FIG. 20, and the average strain at break for these specimens is illustrated in FIG. 21.

Figure 20:
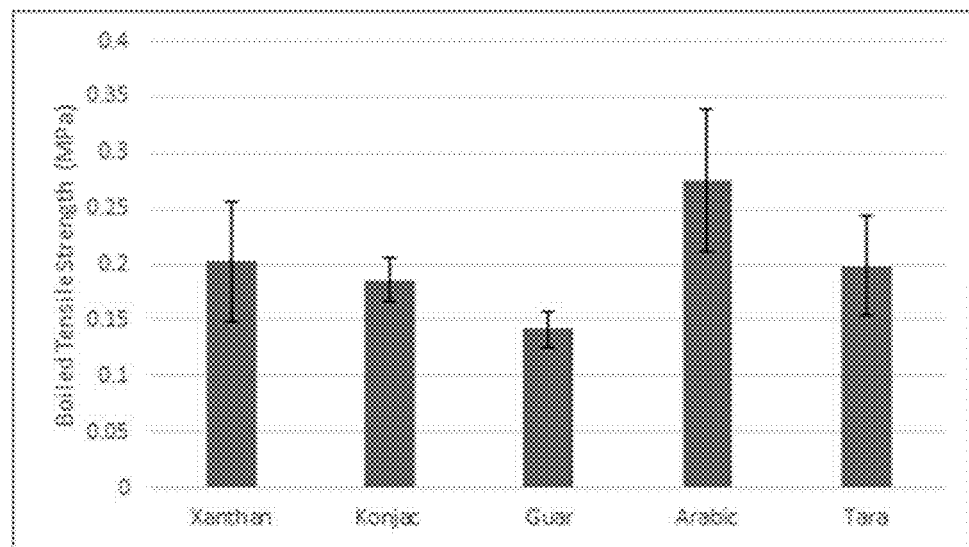
FIG. 20 is a graph showing the effect of AMC thickener on biomat tensile strength.
Figure 21:
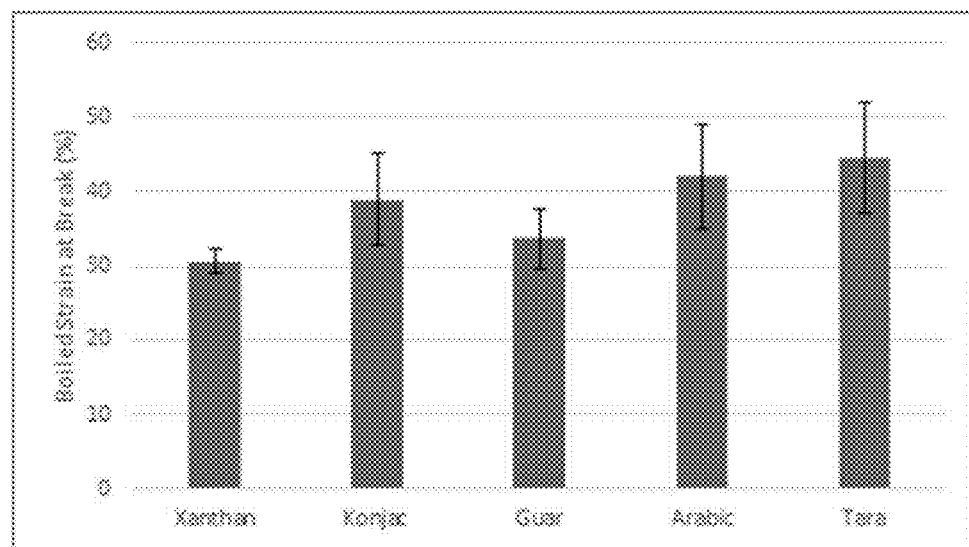
FIG. 21 is a graph showing the effect of AMC thickener on biomat strain at break.

As FIG. 20 illustrates, the tensile strength of boiled biomats was fairly consistent across all thickeners used. Two outliers in this regard are the mats grown on a guar gum AMC, which had notably lower tensile strength than the other mats, and the mats grown on an arabic gum AMC, which had notably higher tensile strength than the other mats; without wishing to be bound by any particular theory, it is hypothesized that the relatively high tensile strength of the latter is due to the thinness of these mats. It was also observed that in addition to having lower tensile strength, mats produced on guar gum AMCs were subjectively more brittle than other mats, possibly due to drying more during mat growth. As FIG. 21 illustrates, strain at break is again fairly consistent across all thickeners used, but it is observed that there is a negative correlation between mat density and strain at break; without wishing to be bound by any particular theory, it is believed that mats of lower density have greater interior void space and thus a lower degree of entanglement or interconnection between fungal filaments, allowing for greater motion of filaments relative to each other when a stress is applied.

Example 19

This Example illustrates the effects of the thickener used to prepare the AMCs on which fungal biomats are grown on the tensile strength and strain at break of the resulting boiled biomats, and in particular the effect of a combined xanthan gum/CMC thickener as compared to xanthan gum alone.

Biomats were produced according to the procedure described in Example 8, except that the amount of fructose in each batch of growth medium was 15% w/v and all batches were aerated using a high-speed disperser at 5,000 rpm; in this Example, the variable that differentiated the AMCs was that half of the AMC samples (nine of 18) contained only 0.4% w/v xanthan gum, while the other half contained both 0.4% w/v xanthan gum and 0.5% w/v CMC (both added during aeration/mixing until fully dissolved). It was observed that the addition of both CMC and xanthan gum resulted in a more viscous AMC than using xanthan gum alone.

The tensile strength and strain at break of the biomats produced was measured according to the procedure described in Example 11. The results are given in Table 8.

TABLE 8

| Sample ID | Thickener (all % w/v) | Strain at break (%) | Tensile strength (kPa) |
|---|---|---|---|
| 1 | Xanthan gum only | 20.031 | 250 |
| 2 | Xanthan gum only | 18.476 | 234 |
| 3 | Xanthan gum only | 19.628 | 353 |
| 4 | Xanthan gum only | 21.679 | 148 |
| 5 | Xanthan gum only | 12.968 | 116 |
| 6 | Xanthan gum only | 20.813 | 210 |
| 7 | Xanthan gum only | 18.519 | 148 |
| 8 | Xanthan gum only | 21.510 | 268 |
| 9 | Xanthan gum only | 17.462 | 246 |
| 10 | Xanthan gum + CMC | 41.818 | 293 |
| 11 | Xanthan gum + CMC | 42.970 | 313 |
| 12 | Xanthan gum + CMC | 45.560 | 285 |
| 13 | Xanthan gum + CMC | 41.722 | 249 |
| 14 | Xanthan gum + CMC | 40.814 | 292 |
| 15 | Xanthan gum + CMC | 40.211 | 215 |
| 16 | Xanthan gum + CMC | 45.951 | 248 |
| 17 | Xanthan gum + CMC | 45.507 | 244 |
| 18 | Xanthan gum + CMC | 25.665 | 212 |
| Average | Xanthan gum only | 19.010 | 219 |
| Average | Xanthan gum + CMC | 41.135 | 261 |

As the results given in Table 8 indicate, addition of CMC in addition to xanthan gum resulted in improvements in the strength of the biomat (average 116% improvement in strain at break and 19% improvement in tensile strength). This allows for more forceful or energy-intensive post-processing steps, e.g. to transform the biomat into a textile or structural material, without risking breakage, rupture, or tear of the biomat.

Example 20

This Example illustrates significant morphological differences between biomats grown on AMCs and those grown on conventional liquid surface fermentation media.

5 μm cross-sections of the mats grown on the 15 wt % fructose media (both AMC and LSF) of Example 8 were taken and stained, then examined by visible light microscopy to examine differences in morphological structure between such samples. Photomicrographs of the mat grown on the LSF medium are shown in FIGS. 22A through 22D, and photomicrographs of the mat grown on the AMC medium are shown in FIGS. 23A through 23D.

Figure 22A:
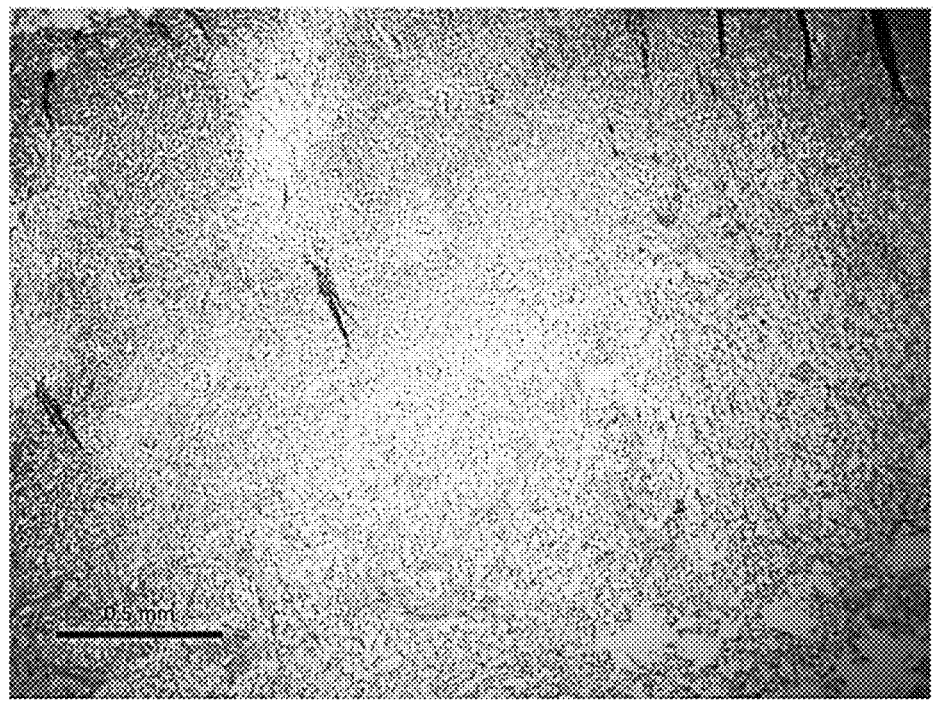
FIG. 22A is a light microscopy image at 40× magnification of a 5 µm cross-section of a biomat grown on a conventional liquid surface fermentation medium containing 15 wt % fructose.
Figure 22B:
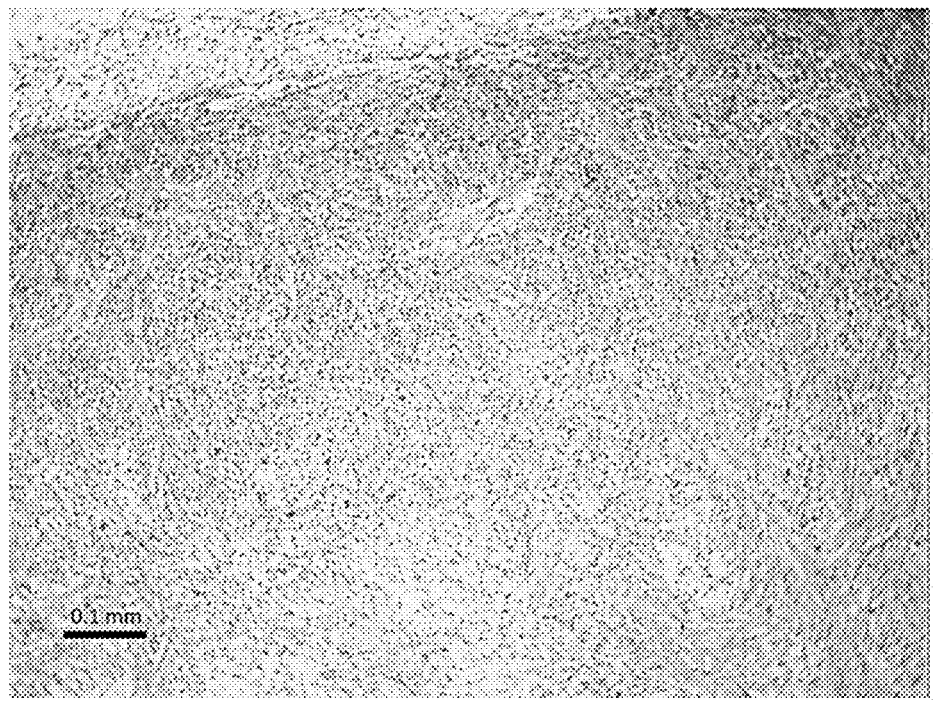
FIGS. 22B, 22C, and 22D are light microscopy images at 100× magnification of bottom (medium-side), middle, and top (hyphal-side) sections of a 5 µm cross-section of a biomat grown on a conventional liquid surface fermentation medium containing 15 wt % fructose.
Figure 22C:
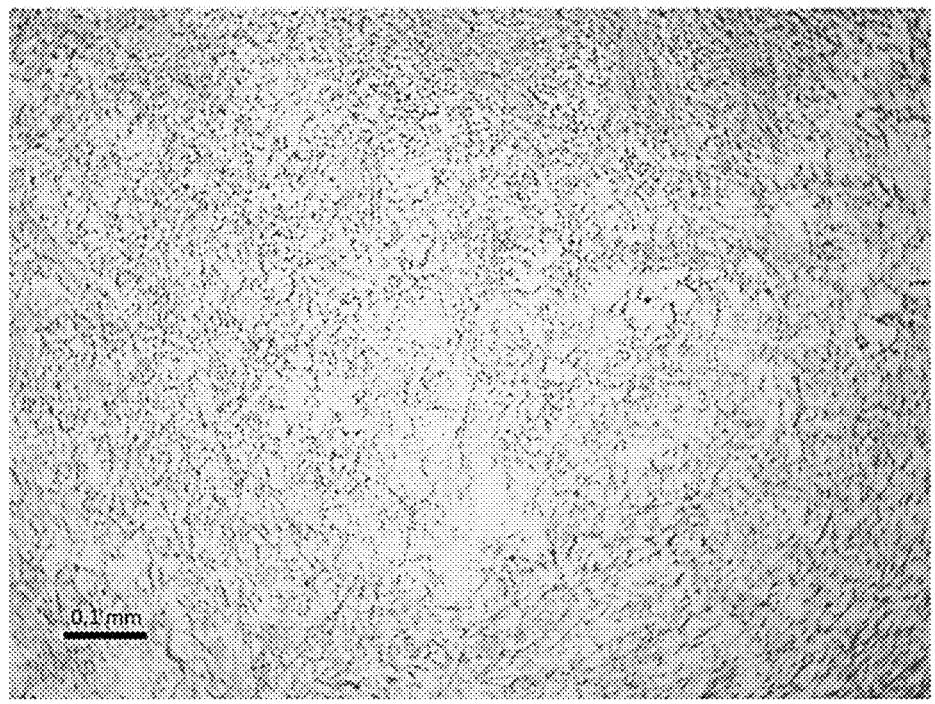
Figure 22D:
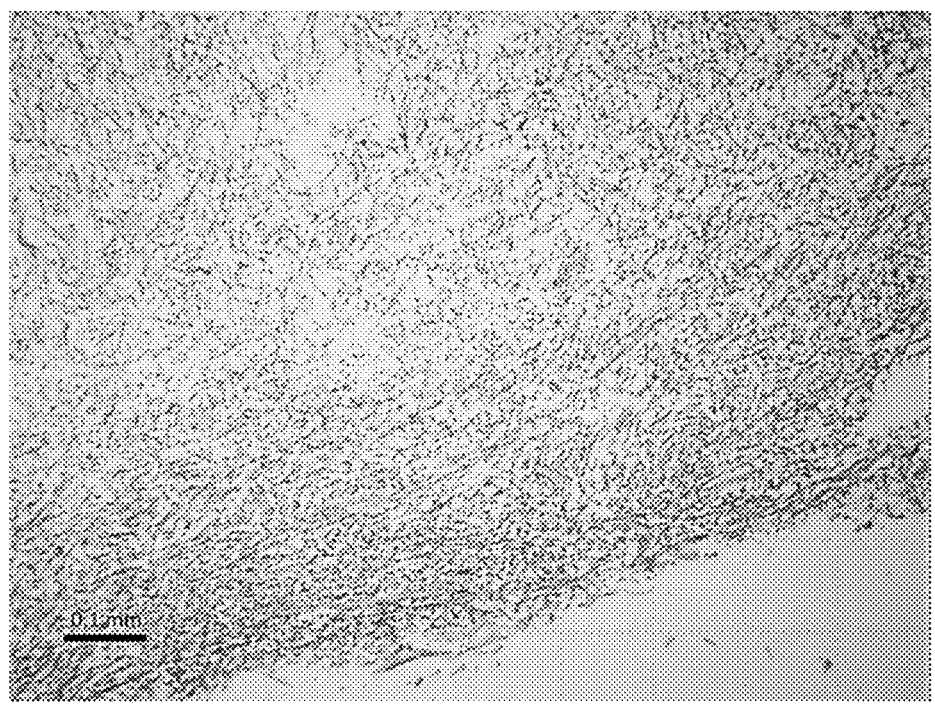

Comparison of the photomicrographs of FIGS. 22A through 23D reveals some striking, and important, differences in the morphology of the mats obtained. The mat grown on the conventional LSF medium has a more homogeneous morphology, with a gradual decrease in filament density from the medium side (FIG. 22B and top of FIG. 22A) to the hyphal side (FIG. 22D and bottom of FIG. 22A). By contrast, the mat grown on the AMC shows three very clearly observable morphological layers: a layer of very dense filaments on the medium side (FIG. 23B and top of FIG. 23A), a somewhat less dense layer on the hyphal side (FIG. 23D and bottom of FIG. 23A), and, between these layers in the interior of the mat, a layer of relatively sparse filament growth and significant void space (FIG. 23C and middle of FIG. 23A).

Figure 23A:
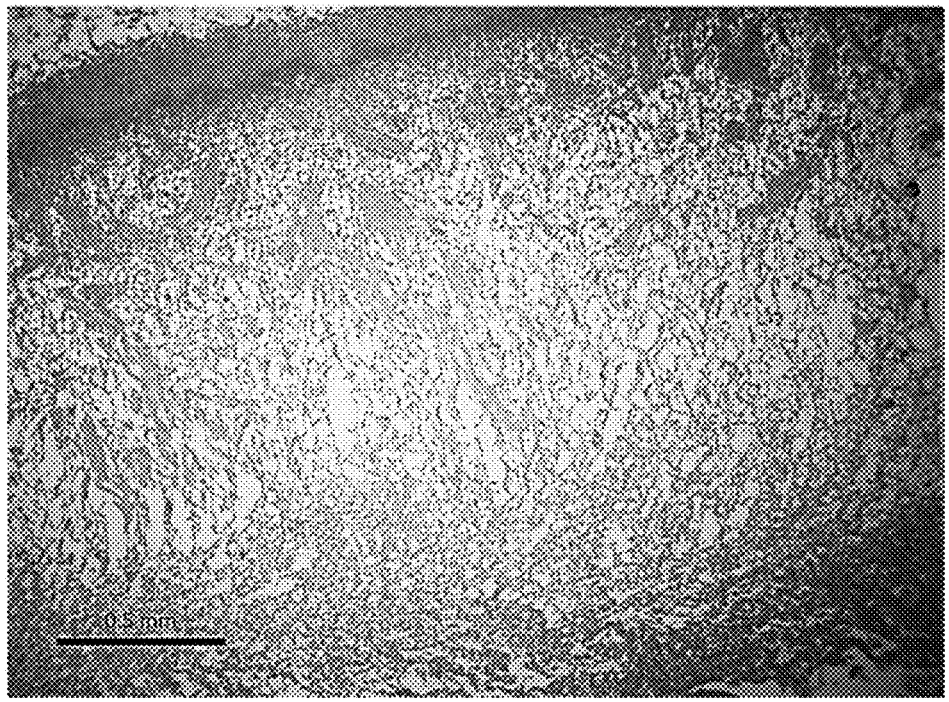
FIG. 23A is a light microscopy image at 40× magnification of a 5 µm cross-section of a biomat grown on an AMC medium containing 15 wt % fructose.
Figure 23B:
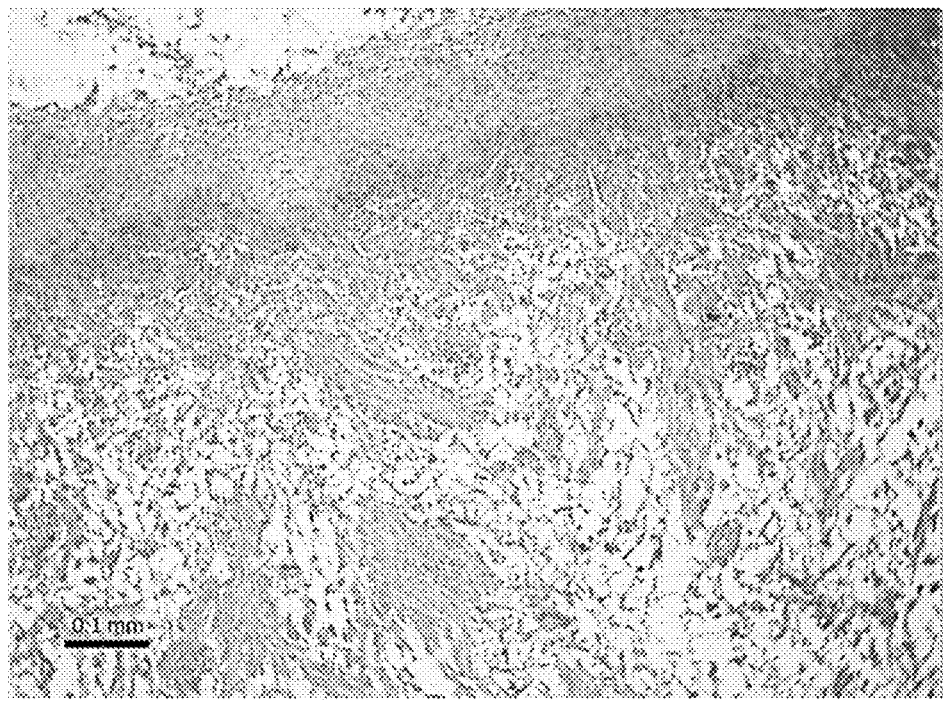
FIGS. 23B, 23C, and 23D are light microscopy images at 100× magnification of bottom (medium-side), middle, and top (hyphal-side) sections of a 5 µm cross-section of a biomat grown on an AMC medium containing 15 wt % fructose.
Figure 23C:
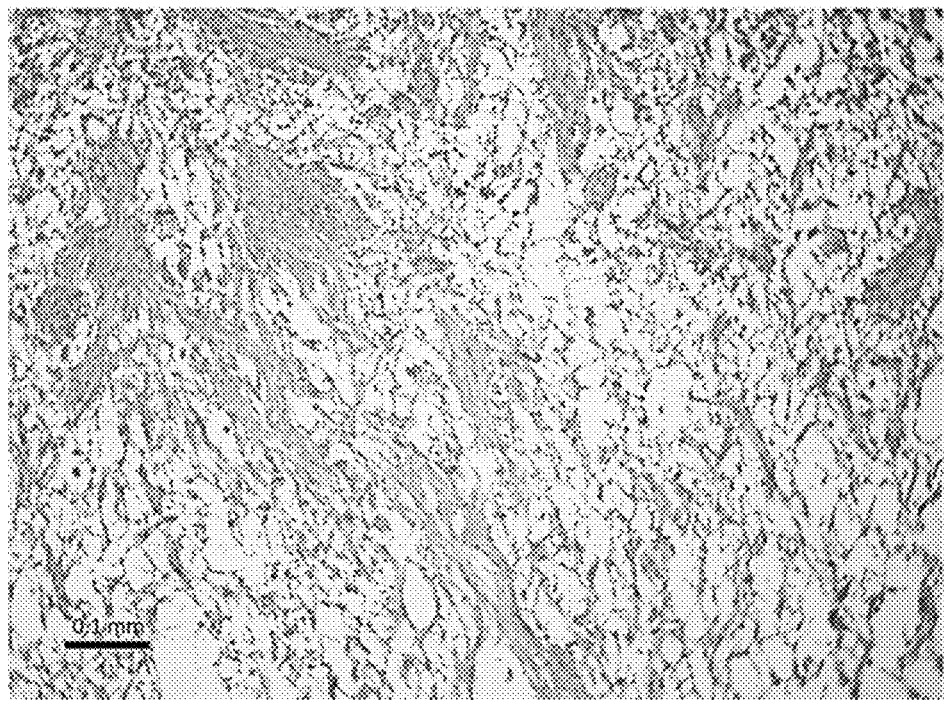
Figure 23D:

Without wishing to be bound by any particular theory, it is believed that the layered morphology of biomats grown on AMCs according to the present invention can confer several advantages because the different morphologies of layers have different properties. By way of first non-limiting example, after harvesting of biomats, one can "shave" or otherwise selectively remove or separate one or more layers, e.g. a dense medium-side layer as illustrated in FIG. 23B, from the biomat and thereby obtain two or more fungal materials having different morphologies, suitable for producing two or more different products (e.g. foodstuffs having different nutritional profiles, foodstuffs or textiles having different textural properties, structural materials or textiles having different mechanical properties, or a combination of these), from a single biomat production run. By way of second non-limiting example, the relative paucity of filaments in the interior portion of the mat may reduce the degree to which filaments are entangled with each other and therefore allow a greater degree of movement of filaments or layers of the biomat relative to each other, which in turn may improve the mechanical characteristics (e.g. tensile strength or strain at break) of the biomat as a whole.

Example 21

This Example illustrates the effect of the stabilizer content of an AMC on the overrun and drainage rate of the AMC, and in turn the effect of these parameters on biomat yield.

Four samples of a fructose-based fermentation medium were prepared and aerated to form an AMC; the samples were identical except that varying amounts of xanthan gum were added to each sample to stabilize the AMC. The pH of each AMC was adjusted to 3.25. The density of each medium prior to aeration was measured as 1.174 g/mL, and the overrun (i.e. the increase in volume of the AMC relative to the volume of fermentation medium used) was measured immediately after AMC preparation by measuring the density of the AMC and comparing this to the density of the original fermentation medium. The drainage rate (i.e. the volume of free liquid generated under the foam per unit time) was recorded one hour after AMC preparation. The viscosity of the AMC was measured at 25° C. two hours after AMC preparation. Subsequently, 1750 g of each medium sample was inoculated with a filamentous fungus inoculum and incubated for 72 hours at 27° C. and 85% relative humidity, and the yield of the resulting biomats was recorded. Results are given in Table 9.

TABLE 9

| Xanthan wt % | Area yield (g/m²) Wet | Dry | % solids | AMC density (g/mL) | Overrun (%) | Drainage rate (mL/hr) | Viscosity (cP) |
|---|---|---|---|---|---|---|---|
| 0.3 | 1120 | 295 | 26.22 | 0.446 | 62.01 | 15.0 | 11250 |
| 0.4 | 1400 | 335 | 24.00 | 0.402 | 65.76 | 7.5 | 10950 |
| 0.5 | 1370 | 351 | 25.70 | 0.438 | 62.69 | 5.0 | 7650 |
| 0.6 | 1530 | 411 | 26.80 | 0.413 | 64.82 | 1.5 | 6550 |

As Table 9 shows, increasing stabilizer content in the AMC results in decreased drainage rate (i.e. increased foam stability) and decreased viscosity. In turn, these material characteristics of the AMC are strongly associated with an increase in the area yield of dry biomat produced.

The invention illustratively disclosed herein suitably may be practiced in the absence of any element which is not specifically disclosed herein. It is apparent to those skilled in the art, however, that many changes, variations, modifications, other uses, and applications of the invention are possible, and also changes, variations, modifications, other uses, and applications which do not depart from the spirit and scope of the invention are deemed to be covered by the invention, which is limited only by the claims which follow.

The foregoing discussion of the invention has been presented for purposes of illustration and description. The foregoing is not intended to limit the invention to the form or forms disclosed herein. In the foregoing Detailed Description of the Invention, for example, various features of the invention are grouped together in one or more embodiments for the purpose of streamlining the disclosure. The features of the embodiments of the invention may be combined in alternate embodiments other than those discussed above. This method of disclosure is not to be interpreted as reflecting an intention that the claimed invention requires more features than are expressly recited in each claim. Rather, as the following claims reflect, inventive aspects lie in less than all features of a single foregoing disclosed embodiment. Thus, the following claims are hereby incorporated into this Detailed Description of the Invention, with each claim standing on its own as a separate preferred embodiment of the invention.

Moreover, though the description of the invention has included description of one or more embodiments and certain variations and modifications, other variations, combinations, and modifications are within the scope of the invention, e.g. as may be within the skill and knowledge of those in the art, after understanding the present disclosure. It is intended to obtain rights which include alternative embodiments to the extent permitted, including alternate, interchangeable, and/or equivalent structures, functions, ranges, or steps to those claimed, whether or not such alternate, interchangeable, and/or equivalent structures, functions, ranges, or steps are disclosed herein, and without intending to publicly dedicate any patentable subject matter.

The invention claimed is:

1. A filamentous fungal biomat having a dry density of at least about 0.20 g/cm³ and a tensile strength of at least about 255 kPa, produced by a method comprising:
   (a) aerating a fermentation medium to provide an air-medium colloid (AMC); and
   (b) culturing a filamentous fungus in or on the AMC to form a biomass of the filamentous fungus in the form of a coherent mat.

2. The biomat of claim 1, further comprising a stabilizer.

3. The biomat of claim 1, further comprising a food-grade or food-safe additive.

4. The biomat of claim 1, having at least one of the following properties:
   (a) a thickness of at least about 1.75 mm;
   (b) a mass of at least about 295 grams per square meter of a top surface area of the AMC; and
   (c) a carbohydrate content of at least about 47 wt % when dry.

5. The biomat of claim 1, wherein the AMC further comprises an inoculum of the filamentous fungus.

6. The biomat of claim 1, wherein the method further comprises inoculating the AMC with an inoculum of the filamentous fungus.

7. The biomat of claim 1, wherein the AMC further omprises a stabilizer.

8. The biomat of claim 7, wherein the stabilizer is selected from the group consisting of a polysaccharide gum, an anionic surfactant, a cationic surfactant, ceteareth 20, cellulose, diacetyl tartaric esters of mono- and diglycerides (DATEM), a diglyceride, an emulsifying wax, glycerol monostearate, a lecithin, a monoglyceride, a mustard, a non-ionic surfactant, a soap, a sodium phosphate, sodium stearoyl lactylate, a zwitterionic surfactant, a saponin, a starch, a modified starch, a plant protein surfactant, an animal protein surfactant, microparticulates, silica, and combinations and mixtures thereof.

9. The biomat of claim 8, wherein the stabilizer comprises xanthan gum.

10. The biomat of claim 7, wherein a mass ratio of the fermentation medium to the stabilizer in the AMC is between about 100:1 and about 1,000:1.

11. The biomat of claim 10, wherein the mass ratio is between about 166:1 and about 500:1.

12. The biomat of claim 1, wherein a volume fraction of air in the AMC is between about 0.05 and about 0.95.

13. The biomat of claim 12, wherein the volume fraction of air in the AMC is between about 0.3 and about 0.7.

14. The biomat of claim 1, wherein the AMC is a foam that is stable over at least about 1 day.

15. The biomat of claim 14, wherein the foam is stable over at least about 3 days.

16. The biomat of claim 1, wherein the filamentous fungus belongs to an order selected from the group consisting of *Ustilaginales, Russulales, Polyporales, Agaricales, Pezizales*, and *Hypocreales*.

17. The biomat of claim 1, wherein the filamentous fungus belongs to a family selected from the group consisting of *Ustilaginaceae, Hericiaceae, Polyporaceae, Grifolaceae, Lyophyllaceae, Strophariaceae, Lycoperdaceae, Agaricaceae, Pleurotaceae, Physalacriaceae, Omphalotaceae, Tuberaceae, Morchellaceae, Sparassidaceae, Nectriaceae*, and *Cordycipitaceae*.

18. The biomat of claim 1, wherein the filamentous fungus belongs to a species selected from the group consisting of *Ustilago esculenta, Hericulum erinaceus, Polyporous squamosus, Grifola fondosa, Hypsizygus marmoreus, Hypsizygus ulmarius, Calocybe gambosa, Pholiota nameko, Calvatia gigantea, Agaricus bisporus, Stropharia rugosoannulata, Hypholoma lateritium, Pleurotus eryngii, Pleurotus ostreatus, Tuber borchii, Morchella esculenta, Morchella conica, Morchella importuna, Sparassis crispa, Fusarium venenatum*, MK7 ATCC Accession Deposit No. PTA-10698, *Disciotis venosa*, and *Cordyceps militaris*.

19. The biomat of claim 1, wherein the method further comprises, prior to or during step (b), adding a food-grade or food-safe additive to the AMC.

20. A foodstuff comprising the biomat of claim 1.

21. A structural material comprising the biomat of claim 1.

22. A textile material comprising the biomat of claim 1.

* * * * *

UNITED STATES PATENT AND TRADEMARK OFFICE
CERTIFICATE OF CORRECTION

PATENT NO. : 11,466,245 B2
APPLICATION NO. : 17/502448
DATED : October 11, 2022
INVENTOR(S) : Michael John Harney, Richard Eugene Macur and Yuval Charles Avniel It is certified that error appears in the above-identified patent and that said Letters Patent is hereby corrected as shown below:

In the Claims

In Column 34, Line 56, Claim 7, please delete "omprises a stabilizer" and insert --comprises a stabilizer--

Signed and Sealed this
Thirty-first Day of January, 2023

Katherine Kelly Vidal
*Director of the United States Patent and Trademark Office*